United States Patent
Foo et al.

(10) Patent No.: US 10,149,880 B2
(45) Date of Patent: Dec. 11, 2018

(54) FEIJOA FRUIT EXTRACT

(71) Applicants: CALLAGHAN INNOVATION, Lower Hutt (NZ); SOUTHWEST SCIENTIFIC EDITING & CONSULTING L.L.C., Tucson, AZ (US)

(72) Inventors: Lai Yeap Foo, Lower Hutt (NZ); Ronald Ross Watson, Tuscon, AZ (US)

(73) Assignees: CALLAGHAN INNOVATION, Lower Hutt (NZ); SOUTHWEST SCIENTIFIC EDITING & CONSULTING, Tucson, AZ (US)

(*) Notice: Subject to any disclaimer, the term of this patent is extended or adjusted under 35 U.S.C. 154(b) by 742 days.

(21) Appl. No.: 14/407,097

(22) PCT Filed: Jun. 10, 2013

(86) PCT No.: PCT/IB2013/054727
§ 371 (c)(1),
(2) Date: Dec. 11, 2014

(87) PCT Pub. No.: WO2013/186680
PCT Pub. Date: Dec. 19, 2013

(65) Prior Publication Data
US 2015/0157678 A1 Jun. 11, 2015

(30) Foreign Application Priority Data

Jun. 11, 2012 (NZ) ........................................ 600560
Jun. 11, 2012 (NZ) ........................................ 600561

(51) Int. Cl.
| | | |
|---|---|---|
| A61K 36/61 | (2006.01) |
| A61K 31/353 | (2006.01) |
| A61K 31/365 | (2006.01) |
| A61K 31/352 | (2006.01) |
| A61K 31/366 | (2006.01) |
| A61K 31/357 | (2006.01) |
| A23L 33/105 | (2016.01) |

(52) U.S. Cl.
CPC ............ *A61K 36/61* (2013.01); *A23L 33/105* (2016.08); *A61K 31/352* (2013.01); *A61K 31/353* (2013.01); *A61K 31/357* (2013.01); *A61K 31/365* (2013.01); *A61K 31/366* (2013.01); *A61K 2236/00* (2013.01)

(58) Field of Classification Search
None
See application file for complete search history.

(56) References Cited

U.S. PATENT DOCUMENTS

| | | |
|---|---|---|
| 5,741,508 A | 4/1998 | Katsumi et al. |
| 5,972,391 A | 10/1999 | Suzuki et al. |
| 5,985,345 A | 11/1999 | Todd |
| 5,985,352 A | 11/1999 | Todd |
| 6,495,176 B1 | 12/2002 | McGenity et al. |
| 6,652,892 B2 | 11/2003 | McGenity et al. |
| 8,017,147 B2 | 9/2011 | Mazed et al. |
| 8,409,822 B2 | 4/2013 | Trevino et al. |
| 8,628,814 B2 | 1/2014 | Weisberg |
| 2005/0129788 A1 | 6/2005 | Agreda Navajas et al. |
| 2007/0128212 A1 | 6/2007 | Sano et al. |
| 2007/0134402 A1 | 6/2007 | Feder |
| 2008/0206372 A1 | 8/2008 | Agreda Navajas et al. |
| 2008/0268073 A1 | 10/2008 | Sano et al. |
| 2009/0151032 P1 | 6/2009 | Hart |
| 2009/0158474 P1 | 6/2009 | Hart |
| 2009/0158475 P1 | 6/2009 | Hart |
| 2009/0252758 A1 | 10/2009 | Mazed et al. |
| 2009/0252796 A1 | 10/2009 | Mazed et al. |
| 2009/0275656 A1 | 11/2009 | Pero |
| 2011/0274680 A1 | 11/2011 | Mazed et al. |
| 2011/0300197 A1 | 12/2011 | McGenity et al. |
| 2013/0251874 A1 | 9/2013 | Muller et al. |
| 2013/0338039 A1 | 12/2013 | Mazed et al. |
| 2014/0212453 A1 | 7/2014 | Chang |
| 2014/0234488 A1 | 8/2014 | Chang |

FOREIGN PATENT DOCUMENTS

| | | |
|---|---|---|
| JP | H10-298094 A | 11/1998 |
| RU | 2 336 734 C1 | 10/2008 |
| WO | 1995/004481 A1 | 2/1995 |
| WO | 2007/103688 A2 | 9/2007 |
| WO | 2010/144991 A1 | 12/2010 |
| WO | 2011/044145 A1 | 4/2011 |
| WO | 2012/030841 A2 | 3/2012 |
| WO | 2012/078798 A1 | 6/2012 |

OTHER PUBLICATIONS

Keles (Pharmaceutical Biology (Mar. 2012), vol. 50, No. 3 pp. 315-325).*
Dos Santos Karine Louise et al: "Traditional Knowledge and Management of Feijoa (*Acca sellowiana*) in Southern Brazil", Economic Botany, New York Botanical Garden, Bronx, NY, US, vol. 63, No. 2, Jun. 1, 2009 (Jun. 1, 2009), pp. 204-214.
Manabe Mariko et al: "Suppressing effects of Feijoa sellowiana Berg (Feijoa) on cytokine secretion by intestinal epithelium", Food Science and Technology Research, vol. 11, No. 1, Feb. 2005 (Feb. 2005), pp. 71-76.
Okuda T; Yoshida T; Hatano T; Yazaki K; Ashida M: "Ellagitannins of the Casuarinaceae Stachyuraceae and Myrtaceae", Phytochemistry., vol. 21, No. 12, Jan. 1, 1982 (Jan. 1, 1982), pp. 2871-2874.
Weston et al: "Bioactive products from fruit of the feijoa (*Feijoa sellowiana, Myrtaceae*): A review", Food Chemistry, Elsevier Ltd, NL, vol. 121, No. 4, Aug. 15, 2010 (Aug. 15, 2010), pp. 923-926.

(Continued)

*Primary Examiner* — Susan Hoffman
(74) *Attorney, Agent, or Firm* — Brian C. Trinque; Benjamin A. Vaughan; Lathrop Gage LLP

(57) ABSTRACT

The invention relates to a *feijoa* fruit extract. In particular the invention relates to therapeutic uses of a *feijoa* fruit extract, processes for preparing the extract, and compositions comprising the extract. The *feijoa* fruit extract of the invention can be used in the treatment and prevention of rheumatoid arthritis and Type-2 diabetes.

17 Claims, 3 Drawing Sheets

(56) References Cited

OTHER PUBLICATIONS

Extended European Search Report corresponding to International Application No. PCT/IB2013054727 dated Oct. 28, 2015.

Haqqi et al. (1999) "Prevention of collagen-induced arthritis in mice by a polyphenolic fraction from green tea," Proc. Natl. Acad. Sci. USA. 96:4524-4529.

John et al. (2011) "Immunomodulatory activity of polyphenols derived from Cassia auriculata flowers in aged rats," Cell. Immunol. 271:474-479.

Peng et al. (2005) "Antihypertensive and cognitive effects of grape polyphenols in estrogen-depleted, female, spontaneously hypertensive rats," Am. J. Physiol. Regul. Integr. Comp. Physiol. 289:R771-R775.

Shukla et al. (2008) "Consumption of Hydrolyzable Tannins Rich Pomegranate Extract (POMx) Suppresses Inflammation and Joint Damage in Rheumatoid Arthritis," Nutrition. 24(7-8):733-743.

Ielpo et al. (2000) "Immunopharmacological properties of flavonoids," Fitorerapia. 71(Suppl 1):S101-S109.

Keles et al. (Mar. 2012) "The effects of Feijoa sellowiana fruits on the antioxidant defense system, lipid peroxidation, and tissue morphology in rats," Pharmaceutical Biology. 50:318-325.

Khoddami et al. (Feb. 2013) "Techniques for Analysis of Plant Phenolic Compounds," Molecules. 18:2328-2375. (published after the earliest priority date of the present application).

Nakashima (2001) "Biological Activity of Feijoa Peel Extracts," Kagoshima University Research Centre for the Pacific Islands, Occasional Papers. No. 34. pp. 169-175.

Rossi et al. (2007) "Inhibition of Inducible Nitric Oxide Synthase Expression by an Acetonic Extract from Feijoa sellowiana Berg. Fruits," Journal of Agricultural and Food Chemistry. 55:5053-5061.

Taghavi et al. (Sep. 2012) "Effect of Feijoa Supplementation in Patients with Type-2 Diabetes," Iranian Journal of Endocrinology and Metabolism. vol. 14. No. 3.—with English abstract.

Vuotto et al. (2000) "Antimicrobial and antioxidant activities of Feijoa sellowiana fruit," International Journal of Antimicrobial Agents. 13:197-201.

Wissam et al. (May 2012) "Effective Extraction of Polyphenols and Proanthocyanidins from Pomegranate's Peel," International Journal of Pharmacy and Pharmaceutical Sciences. 4(Suppl 3):675-682.

International Search Report with Written Opinion corresponding to International Patent Application No. PCT/IB2013/054727, dated Sep. 26, 2013.

International Preliminary Report on Patentability and Written Opinion of the International Searching Authority corresponding to International Patent Application No. PCT/IB2013/054727, dated Dec. 16, 2014.

Wang et al. (2009) "The function, modification and application of dietary fiber," Journal of Henan University of Technology (Natural Science Edition). 30(2):89-94.—Partial English Translation.

* cited by examiner

*FEIJOA* FRUIT EXTRACT

RELATED APPLICATIONS

This application is a 371 filing of Patent Cooperation Treaty Application No. PCT/IB2013/054727, filed Jun. 10, 2013, which claims priority to New Zealand Patent Application Nos. 600560, filed Jun. 11, 2012 and 600561, filed Jun. 11, 2012, the contents of each of which are incorporated herein by reference in their entirety.

1. TECHNICAL FIELD

The invention relates to a *feijoa* fruit extract. In particular the invention relates to therapeutic uses of a *feijoa* fruit extract, a process for preparing the extract, and compositions comprising the extract.

2. BACKGROUND

Diabetes mellitus and obesity have become major global health concerns. Approximately 7% of the American population are affected by diabetes, and 600 million people were estimated to be obese in 2010. The number of people affected by these conditions is expected to increase substantially over the next 25 years.

Type-2 diabetes is the most common form of diabetes and accounts for 90% of all cases. Type-2 diabetes increases the risk of cardiovascular morbidity and mortality, due to the detrimental vascular effects of prolonged exposure to a hyperglycemic environment, as well as the higher prevalence of associated cardiovascular risk factors: atherosclerosis, hypertension, and clotting abnormalities.

Sufferers are often overweight and suffer from hypertension (high blood pressure) and hyperlipidaemia (elevated or abnormal blood lipid levels). These conditions have a major impact on the well-being and lifestyle of sufferers. Hyperglycemia sustained over a prolonged period of time can cause severe damage to the eyes, kidneys, nerves, and pose an increased risk of further complications such as heart attack, stroke, amputation of lower limbs and death. Risks of hyperlipidaemia from diabetes can include pancreatitis, plaque formation, hardening of the arteries and an increased risk of cardiovascular disease.

Obesity is a key contributor to Type-2 diabetes. At present, current obesity treatments, except for surgical removal of the tissue, have failed to result in a sustained reduction of obesity. Furthermore, drugs used for treating obesity may have serious side effects.

Treatment initially involves changes in lifestyle, diet, or the administration of oral medications. Patients are often treated non-specifically which results in undesirable side-effects such as diarrhoea and nausea. The search for new treatments remains ongoing. Natural products and extracts occupy a special place in the market as such treatments are thought to be less toxic and more acceptable to the general population than pharmaceutical therapies.

Rheumatoid arthritis has also become a major global health concern. Approximately 1% of the American population are affected by rheumatoid arthritis. The number of people affected by this condition is expected to increase substantially over the next 25 years.

Rheumatoid arthritis is a systemic autoimmune disease characterised by the chronic inflammation and destruction of joints and surrounding tissue. It is associated with increased mortality. The exact origin of rheumatoid arthritis onset remains unknown. However, rheumatoid arthritis involves a systemic imbalance between pro- and anti-inflammatory cytokine activities, causing the induction of chronic inflammation and joint damage. Therefore, most therapeutic agents for RA have been designed to modulate cytokine levels; for example, tumour necrosis factor-α (TNF-α) and interleukin-1 (IL-1) receptor antagonists have shown promising activity in the prevention of joint destruction by RA. However, humoral immune suppressions by antagonists exhibit therapeutic effects only for a limited period. Treatment for rheumatoid arthritis is often long term, involving both medication and physical therapy.

Some research suggests a connection between rheumatoid arthritis and Type-2 diabetes. People with rheumatoid arthritis show an increased risk of insulin resistance and Type-2 diabetes (Wasko M. C.; Kay, J.; Hsia, H. C. and Rahman, M. U. *Arthritis Care Res* (*Hoboken*) 2011, 63(4):512-21).

The link may be due to the inflammation that occurs with rheumatoid arthritis, which may cause insulin resistance. Some drugs used to treat rheumatoid arthritis may also increase the risk of Type-2 diabetes. Steroids such as prednisone can induce Type-2 diabetes in those already at risk of it. The symptoms of rheumatoid arthritis may also contribute. Joint pain and general fatigue discourage physical exercise making it harder for subjects to maintain cardiovascular fitness and manage weight gain.

There is therefore a need for alternative therapies that can help prevent and manage these conditions. It is an object of the invention to provide a natural fruit extract that goes at least some way towards meeting this need, or at least provides the public with a useful choice.

3. SUMMARY OF INVENTION

The invention generally provides uses of *feijoa* fruit extract in medicinal applications associated with the treatment of Type-2 diabetes and related conditions, and the treatment of rheumatoid arthritis and related conditions. The *feijoa* extract of the invention can be used to treat both conditions simultaneously, or can be used to alleviate symptoms in a subject with rheumatoid arthritis, while simultaneously reducing the risk that the subject will develop Type-2 diabetes.

In a first aspect, the invention provides a method of lowering serum lipids in a patient, comprising administering to the patient an effective amount of *feijoa* fruit extract. The patient may be a human patient with Type-2 diabetes.

In a second aspect, the invention provides a method of lowering serum glucose in a patient, comprising administering to the patient an effective amount of *feijoa* fruit extract. The patient may be a human patient with Type-2 diabetes.

In a third aspect, the invention provides a method of lowering blood pressure in a patient, comprising administering to the patient an effective amount of *feijoa* fruit extract. The patient may be a human patient with Type-2 diabetes.

In a fourth aspect, the invention provides a method of preventing or treating a disease or disorder in a human patient with Type-2 diabetes where it is desirable to lower blood pressure, comprising administering to the human patient an effective amount of *feijoa* fruit extract. The disease or disorder may be hypertension or any disease or disorder associated with elevated blood pressure.

In a fifth aspect, the invention provides a method of preventing or treating a disease or disorder in a human patient with Type-2 diabetes where it is desirable to lower blood lipids, for example cholesterol and triglycerides, comprising administering to the human patient an effective amount of *feijoa* fruit extract. The disease or disorder may be hyperlipidaemia or any other disease or disorder associated with elevated blood lipids.

In a sixth aspect, the invention provides a method of preventing or treating a disease or disorder in the human patient with Type-2 diabetes where it is desirable to lower blood glucose, comprising administering to a human patient an effective amount of *feijoa* fruit extract. The disease or disorder may be hyperglycemia or any other disease or disorder associated with elevated blood glucose levels. The invention further provides a method of reducing HbA1c level in the patient, comprising administering to a patient an effective amount of *feijoa* fruit extract. The patient may be a human patient with Type-2 diabetes.

In an seventh aspect, the invention provides a method of ameliorating the symptoms of diabetes associated with hyperglycemia, hyperlipidaemia and/or hypertension in a human patient with Type-2 diabetes, comprising administering to the human patient an effective amount of *feijoa* fruit extract.

In an eighth aspect, the invention provides a method of ameliorating the symptoms of metabolic syndrome associated with hyperglycemia, hyperlipidaemia and/or hypertension in a human patient, comprising administering to the human patient an effective amount of *feijoa* fruit extract. The patient may be a human patient with Type-2 diabetes.

In a ninth aspect the invention provides a method for preventing or reducing obesity in a patient. The patient may be a human patient.

In a tenth aspect the invention provides a method for preventing or treating a disease or disorder associated with obesity.

In an eleventh aspect the invention provides a method of reducing hepatic total cholesterol levels in a patient. The patient may be an obese human patient.

In a twelfth aspect, the invention provides a method of ameliorating the symptoms of hyperglycemia, hyperlipidaemia and/or hypertension associated with obesity in a human patient, comprising administering to the human patient an effective amount of *feijoa* fruit extract. The patient may be a human patient with Type-2 diabetes.

In the above aspects, in one embodiment the patient may be suffering from rheumatoid arthritis.

In a thirteenth aspect, the invention provides a method of regulating immune function in a patient, comprising administering to the patient an effective amount of *feijoa* fruit extract.

In a fourteenth aspect, the invention provides a method of treating a disease or disorder associated with immunosenescence in a patient, comprising administering to the patient an effective amount of *feijoa* fruit extract.

In a fifteenth aspect, the invention provides a method of preventing or treating the symptoms of rheumatoid arthritis, comprising administering to the patient an effective amount of *feijoa* fruit extract.

In a sixteenth aspect, the invention provides for a method of reducing the levels of inflammatory cytokines associated with rheumatoid arthritis, comprising administering an effective amount of *feijoa* fruit extract to a patient. The patient may be a human patient with rheumatoid arthritis.

In a seventeenth aspect, the invention provides a method of reducing synovial hyperplasia associated with rheumatoid arthritis, comprising administering an effective amount of *feijoa* fruit extract to a patient. The patient may be a human patient with rheumatoid arthritis.

In another aspect the invention provides the use of *feijoa* fruit extract in the manufacture of a medicament for lowering serum lipids in a patient. The patient may be a human patient with Type-2 diabetes.

In another aspect the invention provides the use of *feijoa* fruit extract in the manufacture of a medicament for lowering serum glucose in a patient. The patient may be a human patient with Type-2 diabetes.

In another aspect the invention provides the use of *feijoa* fruit extract in the manufacture of a medicament for lowering blood pressure in a patient. The patient may be a human patient with Type-2 diabetes.

In another aspect the invention provides the use of *feijoa* fruit extract in the manufacture of a medicament for preventing or treating a disease or disorder where it is desirable to lower blood pressure. The disease or disorder may be hypertension or any disease or disorder associated with elevated blood pressure. The patient may be a human patient with Type-2 diabetes.

In another aspect the invention provides the use of *feijoa* fruit extract in the manufacture of a medicament for preventing or treating a disease or disorder where it is desirable to lower blood lipids, for example cholesterol and triglycerides. The disease or disorder may be hyperlipidaemia or any other disease or disorder associated with elevated blood lipids. The patient may be a human patient with Type-2 diabetes.

In another aspect the invention provides the use of *feijoa* fruit extract in the manufacture of a medicament for preventing or treating a disease or disorder where it is desirable to lower blood glucose. The disease or disorder may be hyperglycemia or any other disease or disorder associated with elevated blood glucose levels. The invention further provides the use of *feijoa* fruit extract in the manufacture of a medicament for reducing HbA1c level in a patient. The patient may be a human patient with Type-2 diabetes.

In another aspect the invention provides the use of *feijoa* fruit extract in the manufacture of a medicament for ameliorating the symptoms of diabetes associated with hyperglycemia, hyperlipidaemia and/or hypertension in a human patient.

In another aspect the invention provides the use of *feijoa* fruit extract in the manufacture of a medicament for ameliorating the symptoms of metabolic syndrome associated with hyperglycemia, hyperlipidaemia and/or hypertension in a human patient. The patient may be a human patient with Type-2 diabetes.

In another aspect the invention the use of *feijoa* fruit extract in the manufacture of a medicament for preventing or reducing obesity in a patient. The patient may be a human patient.

In another aspect the invention provides the use of *feijoa* fruit extract in the manufacture of a medicament for preventing or treating a disease or disorder associated with obesity.

In still another aspect the invention provides the use of *feijoa* fruit extract in the manufacture of a medicament for reducing hepatic total cholesterol levels in a patient. The patient may be an obese human patient.

In another aspect the invention provides the use of *feijoa* fruit extract in the manufacture of a medicament for ameliorating the symptoms of hyperglycemia, hyperlipidaemia and/or hypertension associated with obesity in a human patient. The patient may be a human patient with Type-2 diabetes.

In still another aspect the invention provides *feijoa* fruit extract for use in lowering serum lipids in a patient. The patient may be a human patient with Type-2 diabetes.

In still another aspect the invention provides *feijoa* fruit extract for use in lowering serum glucose in a patient. The patient may be a human patient with Type-2 diabetes In still another aspect the invention provides *feijoa* fruit extract for use in lowering blood pressure in a patient. The patient may be a human patient with Type-2 diabetes.

In still another aspect the invention provides *feijoa* fruit extract for use in preventing or treating a disease or disorder where it is desirable to lower blood pressure. The disease or disorder may be hypertension or any disease or disorder associated with elevated blood pressure. The patient may be a human patient with Type-2 diabetes.

In still another aspect the invention provides *feijoa* fruit extract for use in preventing or treating a disease or disorder where it is desirable to lower blood lipids, for example cholesterol and triglycerides. The disease or disorder may be hyperlipidaemia or any other disease or disorder associated with elevated blood lipids. The patient may be a human patient with Type-2 diabetes.

In still another aspect the invention provides *feijoa* fruit extract for use in preventing or treating a disease or disorder where it is desirable to lower blood glucose. The disease or disorder may be hyperglycemia or any other disease or disorder associated with elevated blood glucose levels. The invention further provides *feijoa* fruit extract for use in reducing HbA1c level in a patient. The patient may be a human patient with Type-2 diabetes.

In still another aspect the invention provides *feijoa* fruit extract for use in ameliorating the symptoms of diabetes associated with hyperglycemia, hyperlipidaemia and/or hypertension in a human patient.

In still another aspect the invention provides *feijoa* fruit extract for use in ameliorating the symptoms of metabolic syndrome associated with hyperglycemia, hyperlipidaemia and/or hypertension in a human patient. The patient may be a human patient with Type-2 diabetes.

In still another aspect the invention provides a *feijoa* fruit extract for use in preventing or treating obesity.

In still another aspect the invention provides a *feijoa* fruit extract for use in preventing or treating a disease or disorder associated with obesity.

In still another aspect the invention provides a *feijoa* fruit extract for use in reducing hepatic total cholesterol levels in a patient. The patient may be an obese human patient.

In still another aspect the invention provides *feijoa* fruit extract for use in ameliorating the symptoms of obesity associated with hyperglycemia, hyperlipidaemia and/or hypertension in a human patient. The patient may be a human patient with Type-2 diabetes.

In still another aspect the invention provides *feijoa* fruit extract for use in regulating immune function in a patient.

In still another aspect the invention provides *feijoa* fruit extract for use in preventing or treating a disease or disorder associated with immunosenescence in a patient.

In another aspect the invention provides the use of *feijoa* fruit extract in the manufacture of a medicament for regulating immune function in a patient.

In another aspect the invention provides the use of *feijoa* fruit extract in the manufacture of a medicament for preventing or treating the symptoms of rheumatoid arthritis.

In another aspect, the invention provides the use of *feijoa* fruit extract for reducing the levels of inflammatory cytokines associated with rheumatoid arthritis, comprising administering an effective amount of *feijoa* fruit extract to a patient. The patient may be a human patient with rheumatoid arthritis.

In another aspect, the invention provides the use of *feijoa* fruit extract for reducing synovial hyperplasia associated with rheumatoid arthritis, comprising administering an effective amount of *feijoa* fruit extract to a patient. The patient may be a human patient with rheumatoid arthritis.

In still another aspect the invention provides *feijoa* fruit extract for use in regulating immune function in a patient.

In another aspect the invention provides *feijoa* fruit extract for use in preventing or treating rheumatoid arthritis.

In another aspect, the invention provides *feijoa* fruit extract for use in lowering inflammatory cytokines associated with rheumatoid arthritis, comprising administering an effective amount of *feijoa* fruit extract to a patient. The patient may be a human patient with rheumatoid arthritis.

In another aspect, the invention provides *feijoa* fruit extract for use in reducing synovial hyperplasia associated with rheumatoid arthritis, comprising administering an effective amount of *feijoa* fruit extract to a patient. The patient may be a human patient with rheumatoid arthritis.

In yet another aspect the invention provides a composition for lowering serum lipids in a patient, comprising an effective amount of *feijoa* fruit extract. The patient may be a human patient with Type-2 diabetes.

In yet another aspect the invention provides a composition for lowering serum glucose in a patient, comprising an effective amount of *feijoa* fruit extract. The patient may be a human patient with Type-2 diabetes.

In yet another aspect the invention provides a composition for lowering blood pressure in a patient, comprising an effective amount of *feijoa* fruit extract. The patient may be a human patient with Type-2 diabetes.

In yet another aspect the invention provides a composition for preventing or treating a disease or disorder where it is desirable to lower blood pressure, comprising an effective amount of *feijoa* fruit extract. The disease or disorder may be hypertension or any disease or disorder associated with elevated blood pressure. The patient may be a human patient with Type-2 diabetes.

In yet another aspect the invention provides a composition for preventing or treating a disease or disorder where it is desirable to lower blood lipids, for example cholesterol and triglycerides, comprising an effective amount of *feijoa* fruit extract. The disease or disorder may be hyperlipidaemia or any other disease or disorder associated with elevated blood lipids. The patient may be a human patient with Type-2 diabetes.

In yet another aspect the invention provides a composition for preventing or treating a disease or disorder where it is desirable to lower blood glucose, comprising an effective amount of *feijoa* fruit extract. The disease or disorder may be hyperglycemia or any other disease or disorder associated with elevated blood glucose levels. The invention further provides a composition for reducing HbA1c level in a patient. The patient may be a human patient with Type-2 diabetes.

In yet another aspect the invention provides a composition for ameliorating the symptoms of diabetes associated with hyperglycemia, hyperlipidaemia and/or hypertension in a human patient, comprising an effective amount of *feijoa* fruit extract.

In yet another aspect the invention provides a composition for ameliorating the symptoms of metabolic syndrome associated with hyperglycemia, hyperlipidaemia and/or hypertension in a human patient, comprising an effective amount of *feijoa* fruit extract. The patient may be a human patient with Type-2 diabetes.

In yet another aspect the invention provides a composition for ameliorating the symptoms of hyperglycemia, hyperlipidaemia and/or hypertension associated with obesity in a human patient, comprising an effective amount of *feijoa* fruit extract. The patient may be a human patient with Type-2 diabetes.

In another aspect the invention provides a composition for preventing or treating obesity, comprising an effective amount of *feijoa* fruit extract.

In another aspect the invention provides a composition for preventing or treating a disease or disorder associated with obesity, comprising an effective amount of *feijoa* fruit extract.

In another aspect the invention provides a composition for reducing hepatic total cholesterol in a patient, comprising an effective amount of *feijoa* fruit extract. The patient may be an obese human patient.

In yet another aspect the invention provides a composition for regulating immune function in a patient, comprising an effective amount of *feijoa* fruit extract.

In yet another aspect the invention provides a composition for preventing or treating a disease or disorder associated with immunosenescence in a patient, comprising an effective amount of *feijoa* fruit extract. In another aspect the invention provides *feijoa* fruit extract for use in the manufacture of a medicament.

In yet another aspect the invention provides a composition for regulating immune function in a patient, comprising an effective amount of *feijoa* fruit extract.

In another aspect the invention provides a composition for preventing or treating rheumatoid arthritis, comprising an effective amount of *feijoa* fruit extract.

In another aspect, the invention provides a composition for reducing the levels of inflammatory cytokines associated with rheumatoid arthritis, comprising an effective amount of *feijoa* fruit extract. The patient may be a human patient with rheumatoid arthritis.

In another aspect, the invention provides a composition for reducing synovial hyperplasia associated with rheumatoid arthritis, comprising an effective amount of *feijoa* fruit extract. The patient may be a human patient with rheumatoid arthritis.

In another aspect the invention provides *feijoa* fruit extract for use in the manufacture of a medicament.

In another aspect the invention provides the use of *feijoa* fruit extract as a medicament.

In yet another aspect, the invention provides a composition comprising *feijoa* fruit extract. The composition may be a food or food product. Alternatively, the composition may be a dietary supplement, such as a nutraceutical or other nutritional composition.

In yet another aspect, the invention provides a pharmaceutical composition comprising *feijoa* fruit extract, admixed with one or more pharmaceutically acceptable excipients.

In a further aspect, the invention provides the use of *feijoa* fruit extract as a nutraceutical, such as a dietary supplement, or as an active ingredient in the preparation of medical or functional foods and beverages.

Preferably the *feijoa* fruit extract used in any of the above-described methods, uses and compositions is provided in the form of a pharmaceutical composition, a nutraceutical, e.g. a dietary supplement, or a food product, e.g. a medical or functional food or beverage.

In one embodiment, the *feijoa* fruit extract comprises at least one compound selected from the group consisting of: catechin, epicatechin, gallocatechin, proanthocyanidins, ellagic acid, pedunculagin, luteolin and related ellagitannins. More preferably the *feijoa* fruit extract comprises two or more compounds selected from the group consisting of: catechin, epicatechin, gallocatechin, proanthocyanidins, ellagic acid, pedunculagin, luteolin and related ellagitannins.

In one embodiment, the *feijoa* fruit extract comprises at least one compound selected from the group consisting of: catechin, epicatechin, gallocatechin, proanthocyanidins, flavones, flavanols, ellagic acid, pedunculagin, and related ellagitannins. More preferably the *feijoa* fruit extract comprises two or more compounds selected from the group consisting of: catechin, epicatechin, gallocatechin, proanthocyanidins, flavones, flavanols, ellagic acid, pedunculagin and related ellagitannins.

In one embodiment, the *feijoa* fruit extract comprises (a) at least one oligomeric proanthocyanidin (b) at least one ellagitannin, and (c) flavone.

In another embodiment, the *feijoa* fruit extract comprises (a) about 40 to about 70 wt % oligomeric proanthocyanidin and (b) about 10 to about 20 wt % ellagitannins.

In one embodiment, the *feijoa* fruit extract comprises pedunculagin.

In one embodiment, the *feijoa* fruit extract comprise at least about 50, 55, 60, 65, 70, 75, 80, 85, 90 or 95 wt % polyphenol compounds.

In one embodiment the *feijoa* fruit extract is prepared by a process including the steps (i) to (vi) defined below.

In another aspect, the invention provides a process for preparing *feijoa* fruit extract, including the steps of:

i) contacting whole *feijoa* fruit, and/or *feijoa* fruit skin, and/or *feijoa* fruit pulp and/or residues of *feijoa* fruit from *feijoa* fruit juicing, with an organic solvent, water or an aqueous/organic solvent to provide an aqueous, organic or aqueous/organic extract and a solid residue; and ii) separating the aqueous, organic or aqueous/organic extract from the solid residue to give a crude aqueous, organic or aqueous/organic *feijoa* fruit extract.

iii) evaporating the crude aqueous, organic or aqueous/organic *feijoa* fruit extract from step (ii) to give a substantially aqueous *feijoa* fruit extract concentrate and a precipitate; and iv) separating the substantially aqueous *feijoa* fruit extract concentrate from the precipitate.

v) contacting the substantially aqueous *feijoa* fruit extract from step (iv) with a polymeric resin to adsorb at least one component from the substantially aqueous *feijoa* fruit extract;

vi) eluting at least one component from the resin with an organic solvent or a mixture of organic solvents to obtain the *feijoa* fruit extract.

4. BRIEF DESCRIPTION OF THE FIGURES

5. DETAILED DESCRIPTION OF THE INVENTION

5.1 Abbreviations

Figure 1:
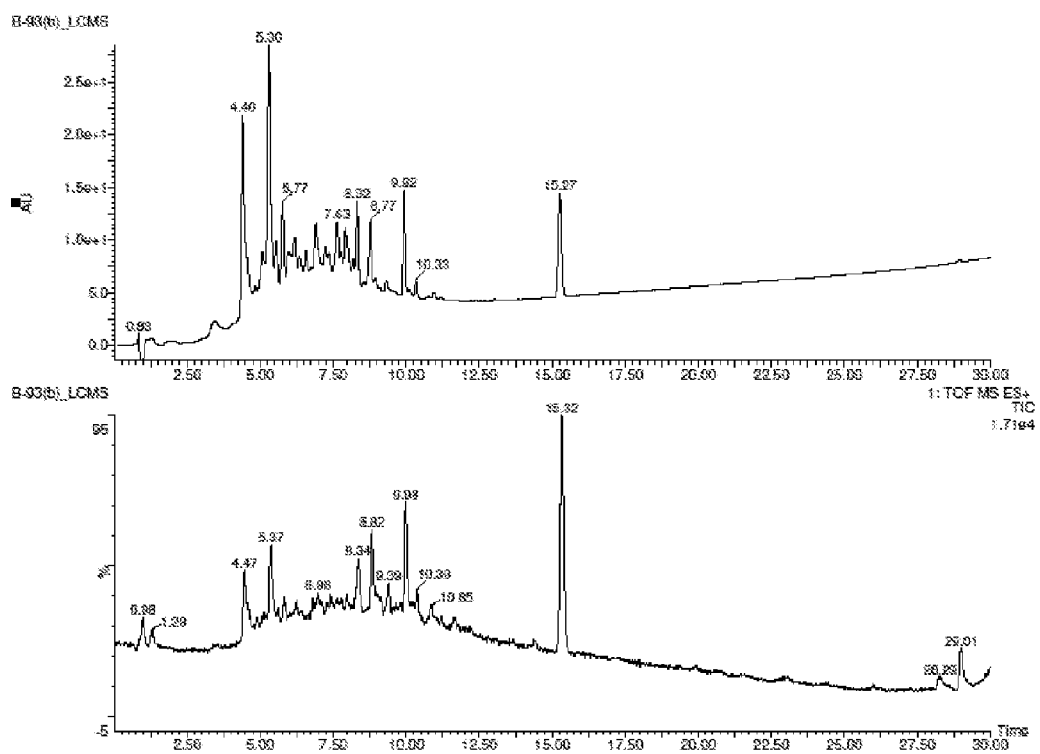
FIG. 1 shows HPLC traces of *feijoa* fruit extract prepared in Example 1 and analysed in Example 2. Upper chromatogram is from diode array detector, lower chromatogram is total ion current (electrospray, positive mode) from mass spectrometer.

ACE Angiotensin-converting enzyme
BP Blood Pressure
CM Culture media
ConA Concanavalin A
CVD Cardiovascular disease
ERK Extracellular signal-regulated kinase
FBS Fetal Bovine Serum
FITC Fluorescein Isothiocyanate
HbA1c Glycosylated Hemoglobin A1c
HCl Hydrochloric acid
HDL High density lipoprotein
IL Interleukin
IFN Interferon
IgG1 Immunoglobulin G1
IκBα Nuclear factor of kappa light polypeptide gene enhancer in B-cells inhibitor, alpha
kg Kilograms
LDL Low density lipoprotein
LPS Lipopolysaccharide
MDA Malondialdehyde
mAb Monoclonal antibody
MI Mitogenesis Index
nM Nano molar
NO Nitric Oxide
PBS Phosphate buffered saline
PE Phycoerythrin
PGE Prostaglandin E2
PHA Phytohemagglutinin
RPMI 1640 A commercial liquid medium

5.2 Definitions

The term "*feijoa* fruit extract" as used herein means an extract of the *feijoa* fruit, including the whole fruit, and/or skin of the *feijoa* fruit and/or *feijoa* fruit pulp and/or residues of *feijoa* fruit remaining after juicing of the fruit (*feijoa* fruit pomace). The fruit or parts thereof may be fresh, frozen (and then thawed) or dried. Juice that is recovered from any processing of the fruit any also be processed to recover a *feijoa* fruit extract.

The term "*feijoa* fruit skin" as used herein means the outer waxy cover of the fruit.

The term "*feijoa* fruit pulp" as used herein means the fleshy contents of the *feijoa* fruit.

The term "*feijoa* fruit pomace" as used herein refers to the fruit residue obtained after juicing of the fruit.

The term "patient" includes human and non-human animals.

The terms "treatment", "treating" and the like include the reduction or alleviation of one or more symptom associated with the disease or disorder. For example, for hyperglycemia, hyperlipidaemia or hypertension this can mean reduction in serum glucose levels, serum lipid levels or blood pressure, respectively.

The terms "preventing", "prevention" and the like include the prevention of one or more symptom associated with the disease or disorder.

The term "comprising" as used in this specification and claims means "consisting at least in part of". When interpreting statements in this specification and claims which include the term "comprising", other features besides the features prefaced by this term in each statement can also be present. Related terms such as "comprise" and "comprised" are to be interpreted in similar manner.

6. DETAILED DESCRIPTION

Research on human nutrition has led to an awareness of the health benefits of dietary supplements. It is recognised that dietary supplements containing complex arrays of naturally occurring bioactive compounds may confer significant long-term health benefits.

*Feijoa sellowiana* Berg syn. *Acca sellowiana*, commonly known as pineapple-guava, is a fruit-bearing evergreen shrub relative of tropical guava. The *feijoa* plant is indigenous to South America but can be found in tropical and subtropical dry areas, particularly in New Zealand. It is grown for its fruit, primarily for the production of juice with a sweet and acidic flavour.

The species has assumed some medicinal relevance due to its content of biologically and nutritionally interesting compounds. A recent review has shown there are no known reports of the effects of *feijoa* consumption on heath, disease prevention or therapy, including diabetes in humans or animals. (Argvelles, M. C., Watson, R. R., *Feijoa* (pineapple-guava) fruit: A role in health promotion? In: R. R. Watson, V. Preedy, editors, Bioactive Foods and Extracts: Cancer Treatment and Prevention, CRC Press, published December 2010, ISBW 1439816190)). However, some studies have shown a high correlation between the total phenol content and the radical scavenging activity of extracts of *feijoa* on cultured cells (Yuka, I., Yumiko, K., Miyo, N., Takashi K., J. Home. Econ. Japan, 2003, 54, 945-949). Therefore, the *feijoa* fruit has joined a growing list of edible plant that are being investigated for their medicinal properties.

The applicants have discovered that *feijoa* fruit extract has efficacy in the treatment and prevention of both diabetes and rheumatoid arthritis.

6.1 The *Feijoa* Fruit Extract

The *feijoa* fruit extract of the invention is prepared by extracting the *feijoa* fruit, including the whole fruit, and/or skin of the *feijoa* fruit and/or *feijoa* fruit pulp and/or residues of *feijoa* fruit remaining after juicing of the fruit.

The extraction process may be prepared using standard extraction techniques known in the art. In one embodiment the *feijoa* fruit extract is prepared by a process including the steps (i) to (vi) defined below.

In one aspect the invention provides a process for preparing *feijoa* fruit extract, including the steps of:
  i) contacting *feijoa* fruit, and/or *feijoa* fruit skin, and/or *feijoa* fruit pulp and/or residues of *feijoa* fruit from *feijoa* fruit juicing, with a hydrophilic organic solvent, water or an aqueous/organic solvent to provide an aqueous, organic or aqueous/hydrophilic organic extract and a solid residue; and
  ii) separating the aqueous, organic or aqueous/organic extract from the solid residue to give a crude aqueous, organic or aqueous/organic *feijoa* fruit extract;

iii) evaporating the crude aqueous, organic or aqueous/organic *feijoa* fruit extract from step (ii) to give a substantially aqueous *feijoa* fruit extract concentrate and a precipitate;

iv) separating the substantially aqueous *feijoa* fruit extract concentrate from the precipitate; and v) fractionating the substantially aqueous *feijoa* fruit extract concentrate from step iv) to concentrate at least one component thereof.

In one embodiment the substantially aqueous *feijoa* fruit extract concentrate from step iv) is fractionated using polymeric resin absorption, chromatographic separation, solvent partitioning or selective precipitation.

In another embodiment the substantially aqueous *feijoa* fruit extract concentrate from step iv) may be dried and dissolved in a mixture of an organic solvent and water, for example 70:30 ethanol:water. The sugars and other polar material are not soluble in this solvent. Drying the organic solvent and water mixture will provide a *feijoa* fruit extract more concentrated in polyphenol compounds. This procedure can be repeated several times.

In another embodiment the substantially aqueous *feijoa* fruit extract concentrate from step iv) may be dissolved in a non-water miscible solvent, such as ethyl acetate or 1-butanol to yield a non-aqueous *feijoa* fruit extract with high polyphenol levels.

In another aspect, the invention provides a process for preparing *feijoa* fruit extract, including the steps of:

i) contacting whole *feijoa* fruit, and/or *feijoa* fruit skin, and/or *feijoa* fruit pulp and/or residues of *feijoa* fruit from *feijoa* fruit juicing, with an organic solvent, water or an aqueous/organic solvent to provide an aqueous, organic or aqueous/organic extract and a solid residue; and ii) separating the aqueous, organic or aqueous/organic extract from the solid residue to give a crude aqueous, organic or aqueous/organic *feijoa* fruit extract;

iii) evaporating the crude aqueous, organic or aqueous/organic *feijoa* fruit extract from step (ii) to give a substantially aqueous *feijoa* fruit extract concentrate and a precipitate;

iv) separating the substantially aqueous *feijoa* fruit extract concentrate from the precipitate;

v) contacting the substantially aqueous *feijoa* fruit extract from step (iv) with a polymeric resin to adsorb at least one component from the substantially aqueous *feijoa* fruit extract;

vi) eluting at least one component from the resin with an organic solvent or a mixture of organic solvents to obtain the *feijoa* fruit extract.

The *feijoa* fruit extract produced by the process of the invention can be vacuum dried, spray dried or freeze-dried to produce a free-flowing powder.

In one embodiment, the *feijoa* fruit extract is a free-flowing powder.

The whole *feijoa* fruit, and/or *feijoa* fruit skin and/or *feijoa* fruit pulp and/or residues of *feijoa* fruit left over after juicing of the fruit may optionally be minced, mashed, crushed, blended, sliced or chopped prior to step (i). The fruit or fruit portions may be frozen and thawed prior to step (i). They may also be dried prior to step (i).

*Feijoa* fruit may be juiced (the juice removed from the fruit by squeezing or other means) prior to step (i), thereby providing said residues of *feijoa* fruit left over after juicing of the fruit, which can be used in step (i). Juicing can be carried out using a centrifuge, screw press or mechanical press, or other method known in the art. The de-juicing operation may be combined with an enzyme pre-treatment to assist in the release of polyphenol compounds from the fruit or parts thereof.

In one embodiment the organic solvent is acetone or an alcohol such as methanol, ethanol, isopropyl alcohol or 1-propanol. Where an aqueous/organic solvent is used, the organic solvent and water can be used in any suitable proportions, such as about 20-90% water.

In one embodiment, the substantially aqueous *feijoa* fruit extract concentrate from step iv) is fractionated by contacting it with a polymeric resin. The resin absorbs at least one component from the extract concentrate. The component(s) can then be eluted from the resin with an organic solvent or mixture of organic solvents to give the *feijoa* fruit extract of the invention.

The polymeric resin may optionally be washed with distilled water prior to eluting the at least one component. In one embodiment, the polymeric resin is a non-ionic polymeric absorbent resin. Preferably the polymeric absorbent resin is a non-iconic styrene-divinyl benzene co-polymer resin such as Mitsubishi HP-20, Mitsubishi Sepabeads SP-70 or Amberlite. Example 1 provides an example of a method of preparing *feijoa* fruit extract of the invention.

*Feijoa* is known to contain high levels of polyphenols. Polyphenols are a widely ranging group of biological molecules that play a protective role in plants. Generally characterised by the presence of multiple and often polyhydroxylated phenol units, there are many different classes of polyphenols, with a huge variety of compounds falling within each class.

Each plant species will have a different and characteristic polyphenol profile which will also vary to an extent depending on the environmental conditions it is grown under. Different processing methods may also provide plant material with different polyphenol profiles. Therefore, it is not feasible to identify all of the polyphenol compounds in an extract of a polyphenol-rich plant. However, chromatographic separation of the fruit extract of the invention leads to the isolation and identification of catechin (III), epicatechin (IV), gallocatechin (V), procyanidin B2 (VI), proanthocyanidin oligomers (VII), ellagic acid, α- and β-pedunculagin as well as other related ellagitannins (see compounds (I) to (VII), below) as characteristic compounds. The components of *feijoa* fruit extract prepared in Example 1 are isolated and identified in Example 2—see Table 1 and FIG. 1 which relate to HPLC traces of *feijoa* fruit extract.

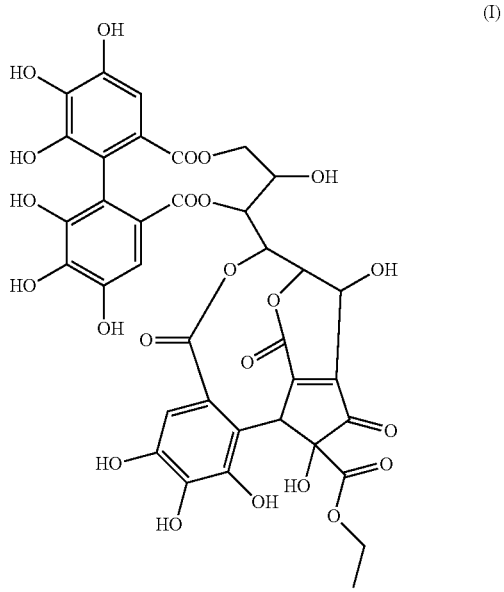

(I)

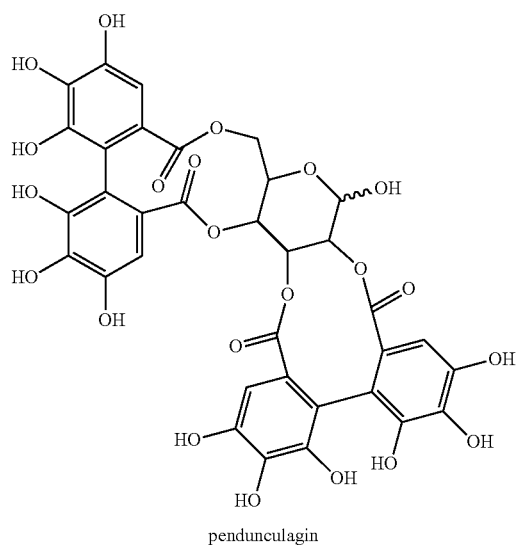

pendunculagin (II)

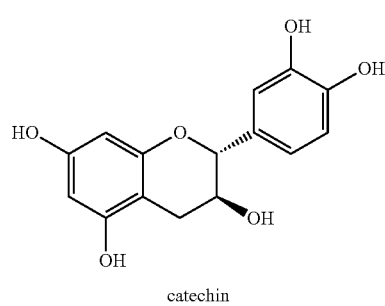

catechin (III)

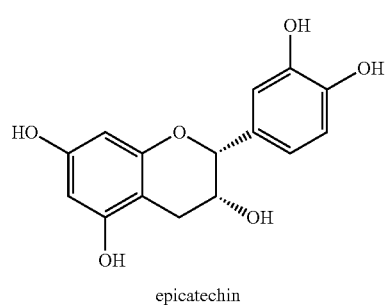

epicatechin (IV)

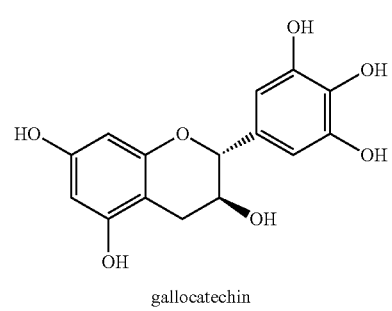

gallocatechin (V)

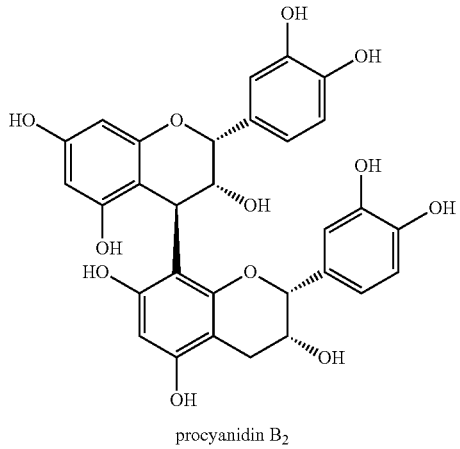

procyanidin B$_2$ (VI)

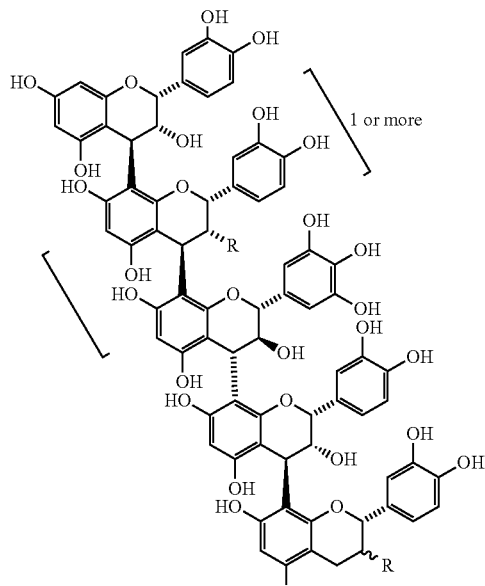

Proanthocyanidin oligomers (VII)

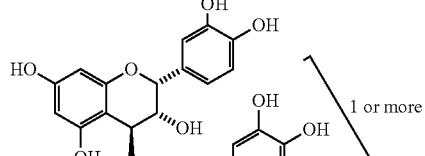

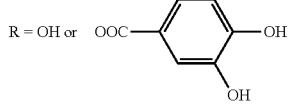

In one aspect, the *feijoa* fruit extract comprises at least one compound selected from the group consisting of: catechin, epicatechin, gallocatechin, proanthocyanidins, flavone, flavanols, ellagic acid, pedunculagin, and related ellagitannins. More preferably the *feijoa* fruit extract comprises two or more compounds selected from the group consisting of: catechin, epicatechin, gallocatechin, proanthocyanidins, flavone, flavanols, ellagic acid, pedunculagin and related ellagitannins.

In particular, the *feijoa* fruit extract of the invention has been shown to contain large proportions of two large polyphenols—oligomeric proanthocyanidins (proanthocyanidin oligomers) and ellagitannins. These two polyphenol classes act together in the extracts of the invention to provide surprising efficacy in the treatment and prevention Type-2 diabetes and rheumatoid arthritis.

In one aspect, the invention provides a *feijoa* fruit extract comprising
(a) about 40 to about 70 wt %, (preferably about 50 to about 60 wt %) oligomeric proanthocyanidin and
(b) about 10 to about 20 wt % ellagitannins, on a dry weight basis.

In other words, when the extract is substantially free of water, about 40 to about 70 wt % of the extract consists of oligomeric proanthocyanidin.

In another aspect, the invention provides a *feijoa* fruit extract comprising (a) about 40 to about 70 wt %, (preferably about 50 to about 60 wt %) oligomeric proanthocyanidin and (b) about 10 to about 20 wt % ellagitannins, on a total polyphenol basis.

In other words, oligomeric proanthocyanidins make up about 40 to about 70 wt % of the total polyphenols present in the extract.

Preferably, the *feijoa* fruit extract comprises pedunculagin and/or flavone.

In one embodiment, the *feijoa* fruit extract comprises at least about 50, 55, 60, 65, 70, 75, 80, 85, 90, or 95 wt % polyphenol compounds, on a dry weight basis. Preferably, the *feijoa* fruit extract comprises about 60 to about 90% polyphenol compounds, on a dry weight basis.

In one embodiment, the *feijoa* fruit extract comprises (a) about 40 to about 70 wt % (preferably about 50 to 60 wt %) oligomeric proanthocyanidin and (b) about 10 to about 20 wt % ellagitannins, wherein the *feijoa* fruit extract comprises about 60 to about 90 wt % (preferably about 70 to about 90 wt %) polyphenol compounds, on a dry weight basis.

In one embodiment, the *feijoa* fruit extract comprises (a) about 40 to about 70 wt % (preferably about 50 to 60 wt %) oligomeric proanthocyanidin and (b) about 10 to about 20 wt % ellagitannins, wherein the *feijoa* fruit extract comprises about 60 to about 90 wt % (preferably about 70 to about 90 wt %) polyphenol compounds.

Advantageously, the *feijoa* fruit extract of the invention can be provided to a patient in a variety of forms. For example, the *feijoa* fruit extract can be provided as a nutraceutical, e.g. a dietary supplement. Alternatively, the *feijoa* fruit extract can be provided as a food product, e.g. as part of a functional food or beverage. The *feijoa* fruit extract of the invention can be provided as an adjunct to conventional treatments. As a natural food ingredient, it is unlikely to produce undesirable side-effects such as interfering with the efficacy of conventional pharmaceutical treatments.

Alternatively, the *feijoa* fruit extract can be provided as a pharmaceutical composition. The extract may be formulated into solid or liquid preparations such as tablets, capsules, suppositories, powders, solutions, suspensions and dispersions. In some embodiments the *feijoa* fruit extract is formulated for oral administration as solid or liquid preparations, for example tablets, capsules, powders, solutions, suspensions or dispersions. Such preparations are well known in the art as are other oral dosage regimes not listed here. In the tablet form the *feijoa* fruit extract may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added.

When aqueous suspensions are required for oral use, the *feijoa* fruit extract may be combined with carriers such as water and ethanol, and emulsifying agents, suspending agents and/or surfactants may be used. Colourings, sweeteners or flavourings may also be added.

The compounds may further be administered by means of sustained release systems. For example, they may be incorporated into a slowly dissolving tablet or capsule.

Liquid forms include carriers such as water and ethanol, with or without other agents such as pharmaceutically acceptable surfactants or suspending agents.

In one aspect the invention provides a dosage unit comprising about 150 mg *feijoa* fruit extract.

In another aspect, the invention comprises a dosage unit consisting essentially of 150 mg *feijoa* fruit extract.

Preferably, the dosage unit is a tablet.

6.2 Use of *Feijoa* Fruit Exact in Regulating Immune Function

Ageing is clearly associated with a decline in immune function and is a major contributing factor to high rates of morbidity and mortality in the elderly. The *feijoa* fruit extract of the present invention is useful for regulating immune function and/or for preventing or treating diseases disorders associated with immunosenescence in a patient.

The effect of the *feijoa* fruit extract of the present invention on the immune function of mice was evaluated in Example 3. Aged mice fed diets supplemented with *feijoa* fruit extract were evaluated for changes in immune function by assessing production of cytokines, mitogenesis of splenocytes and vitamin E levels. IL-2, IL-4, IL-6 and IFN are inflammatory cytokines important in the B-cell production of antibodies and are key components of the adaptive immune system. Aging is a major risk factor for the development of diabetes and its complications and thus reduced inflammatory cytokines also help lower the risk for diabetes. Example 3 demonstrates that the *feijoa* fruit extract supplemented at an appropriate dose causes significant increase in splenic T-cell immune function in aged mice. The *feijoa* fruit extract also increases levels of hepatic vitamin E and lowers TNF-α levels. Low grade chronic inflammation is a common event in the aged and the pro-inflammatory cytokine modulation observed suggest that *feijoa* fruit extract helps to treat chronic inflammation as measured by cytokine changes. Inflammation, typically stimulated by dysregulation in aging or disease with elevated T-helper 2 cytokines, contributes to arthritis and diabetes. Immune dysregulation in aged systems can exacerbate inflammation and thus could accentuate rheumatoid arthritis.

In one aspect, the invention provides a method of regulating immune function in a patient, comprising administering to the patent an effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a dry weight basis.

In another aspect, the invention provides a method of treating a disease or disorder associated with immunosenescence in a patient, comprising administering to the patient an effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a dry weight basis.

In another aspect, the invention provides a method of reducing the levels of inflammatory cytokines in a patient, comprising administering to the patient an effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a dry weight basis.

In one aspect, the invention provides a method of regulating immune function in a patient, comprising administering to the patent an effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a total polyphenol basis.

In another aspect, the invention provides a method of treating a disease or disorder associated with immunosenescence in a patient, comprising administering to the patient an effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a total polyphenol basis.

In another aspect, the invention provides a method of reducing the levels of inflammatory cytokines in a patient, comprising administering to the patient an effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a total polyphenol basis.

In the above aspects:

In one embodiment, the *feijoa* fruit extract comprises about 60 to about 90% polyphenol compounds, on a dry weight basis.

In one embodiment, the *feijoa* fruit extract comprises about 60 to about 90 wt % polyphenol compounds.

In one embodiment, the patient is administered 150 mg of *feijoa* fruit extract daily.

In one aspect, the invention provides a dosage unit for regulating immune function in a patient, wherein the dosage unit comprises about 150 mg *feijoa* fruit extract.

In one embodiment, the dosage unit is a tablet. In one embodiment, the dosage unit is to be administered once daily.

6.3 Use of *Feijoa* Fruit Extract in the Treatment and/or Prevention of Obesity, Type-2 Diabetes and Associated Diseases The *feijoa* fruit extract of the present invention has been shown to be useful in the treatment and/or prevention of diseases and disorders such as those associated with obesity, metabolic syndrome and Type-2 diabetes. Diseases and disorders include those associated with elevated blood pressure, elevated serum glucose levels and/or elevated serum lipid levels, e.g. hyperglycemia, hyperlipidaemia and hypertension.

The applicants have surprisingly shown that supplementation of the diet of Type-2 diabetes patients with *feijoa* fruit extract reduces the patient's blood pressure and results in improved diabetes control. Plasma fasting glucose and HbA1c levels improve and reach statistical significance when compared to a placebo (see Example 4).

Without wishing to be bound by theory, it is thought that the glucose-lowering effect of an extract of *feijoa* might be mediated through the inhibition of α-glucosidase, thus diminishing glucose intestinal resorption. Furthermore, *feijoa* fruit extract of the present invention is useful for preventing or reducing obesity through the suppression of weight gain and lowering of the food efficiency ratio.

The effect of the *feijoa* fruit extract of the present invention on obesity and related lipid driven risk factors in mice was also evaluated (see Example 5). Those mice receiving the *feijoa* fruit extract showed lower body weight gain in comparison to the control group.

In one aspect, the invention provides a method for preventing or treating Type-2 diabetes in a patient, comprising administering to the patient an effective amount of *feijoa* fruit extract. In one embodiment, the patient suffers from rheumatoid arthritis.

In another aspect, the invention provides a method for lowering serum lipids in a patient, comprising administering to the patient an effective amount of *feijoa* fruit extract, wherein the *feijoa* fruit extract comprises (a) about 40 to about 70 wt % (preferably about 50 to about 60 wt %) oligomeric proanthocyanidin and (b) about 10 to about 20 wt % ellagitannins, on a dry weight basis.

In another aspect, the invention provides a method for lowering serum glucose in a patient, comprising administering to the patient an effective amount of *feijoa* fruit extract, wherein the (a) about 40 to about 70 wt % (preferably about 50 to about 60 wt %) oligomeric proanthocyanidin and (b) about 10 to about 20 wt % ellagitannins, on a dry weight basis In another aspect, the invention provides a method for lowering blood pressure in a patient, comprising administering to the patient an effective amount of *feijoa* fruit extract, wherein the (a) about 40 to about 70 wt % (preferably about 50 to about 60 wt %) oligomeric proanthocyanidin and (b) about 10 to about 20 wt % ellagitannins, on a dry weight basis.

In another aspect, the invention provides a method for treating or preventing metabolic syndrome in a patient, comprising administering to the patient an effective amount of *feijoa* fruit extract, wherein the *feijoa* fruit extract comprises (a) about 40 to about 70 wt % (preferably about 50 to about 60 wt %) oligomeric proanthocyanidin and (b) about 10 to about 20 wt % ellagitannins, on a dry weight basis.

In another aspect, the invention provides a method for lowering serum lipids in a patient, comprising administering to the patient an effective amount of *feijoa* fruit extract, wherein the *feijoa* fruit extract comprises (a) about 40 to about 70 wt % (preferably about 50 to about 60 wt %) oligomeric proanthocyanidin and (b) about 10 to about 20 wt % ellagitannins, on a total polyphenol basis.

In another aspect, the invention provides a method for lowering serum glucose in a patient, comprising administering to the patient an effective amount of *feijoa* fruit extract, wherein the (a) about 40 to about 70 wt % (preferably about 50 to about 60 wt %) oligomeric proanthocyanidin and (b) about 10 to about 20 wt % ellagitannins, on a total polyphenol basis.

In another aspect, the invention provides a method for lowering blood pressure in a patient, comprising administering to the patient an effective amount of *feijoa* fruit extract, wherein the (a) about 40 to about 70 wt % (preferably about 50 to about 60 wt %) oligomeric proanthocyanidin and (b) about 10 to about 20 wt % ellagitannins, on a total polyphenol basis.

In another aspect, the invention provides a method for treating or preventing metabolic syndrome in a patient, comprising administering to the patient an effective amount of *feijoa* fruit extract, wherein the *feijoa* fruit extract comprises (a) about 40 to about 70 wt % (preferably about 50 to about 60 wt %) oligomeric proanthocyanidin and (b) about 10 to about 20 wt % ellagitannins, on a total polyphenol basis.

In one embodiment of the above aspects, the patient is a human with Type-2 diabetes.

In another aspect the invention provides a method of treating or preventing Type-2 diabetes in a patient, comprising administering to the patient an effective amount of *feijoa* fruit extract, wherein the *feijoa* fruit extract comprises (a) about 40 to about 70 wt % (preferably about 50 to about 60 wt %) oligomeric proanthocyanidin and (b) about 10 to about 20 wt % ellagitannins, on a dry weight basis.

In another aspect the invention provides a method of treating or preventing Type-2 diabetes in a patient, comprising administering to the patient an effective amount of *feijoa* fruit extract, wherein the *feijoa* fruit extract comprises (a) about 40 to about 70 wt % (preferably about 50 to about 60 wt %) oligomeric proanthocyanidin and (b) about 10 to about 20 wt % ellagitannins, on a total polyphenol basis.

In the above aspects:

In one embodiment, the *feijoa* fruit extract comprises about 60 to about 90% polyphenol compounds, on a dry weight basis.

In one embodiment, the *feijoa* fruit extract comprises about 60 to about 90 wt % polyphenol compounds.

In one embodiment, the patient is administered 150 mg of *feijoa* fruit extract daily.

In one aspect, the invention produces a dosage unit for treating or preventing Type-2 diabetes in a patient, wherein the dosage unit comprises about 150 mg *feijoa* fruit extract.

In one embodiment, the dosage unit is a tablet. In one embodiment, the dosage unit is to be administered once daily.

6.4 Use of *Feijoa* Fruit Extract in the Treatment and/or Prevention of Rheumatoid Arthritis The *feijoa* fruit extract of the present invention is also useful in the treatment and/or prevention of diseases and disorders such as those associated with rheumatoid arthritis.

The effect of the *feijoa* fruit extract of the present invention on induced rheumatoid arthritis in mice is evaluated in Example 6. The collagen-induced arthritis (CIA) model has been used extensively to elucidate the pathogenic mechanisms that are relevant to human rheumatoid arthritis, and is widely used for the evaluation of potential anti-rheumatic agents. The acute stage of CIA is characterised by increased levels of mRNA for pro-inflammatory cytokines in the joints, such as TNF-α, IL-1β, and IFN-γ. Many of the major pro-inflammatory cytokines that are produced in the rheumatoid synovium, are linked to a network or cascade with TNF-α at its apex. IL-1β was previously shown to be important in cartilage and bone destruction.

Histological studies show that *feijoa* fruit extract protects against synovial hyperplasia—an increase in destructive cytokine production in synovial fluid that can facilitate the onset of rheumatoid arthritis. Radiologic studies show that *feijoa* fruit extra protects against joint deformity and soft tissue swelling in CIA mice. *Feijoa* fruit extract supplementation also decreases IL-2 and IFN-γ levels compared to the arthritic control group (see Table 9).

In one aspect the invention provides a method of preventing or treating the symptoms of rheumatoid arthritis, comprising administering to the patient and effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a dry weight basis.

In another aspect of the invention provides a method for reducing the levels of inflammatory cytokines associated with rheumatoid arthritis, comprising administering to the patient and effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a dry weight basis.

In another aspect of the invention provides a method of reducing synovial hyperplasia associated with rheumatoid arthritis, comprising administering to the patient an effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a dry weight basis.

In one aspect the invention provides a method of preventing or treating the symptoms of rheumatoid arthritis, comprising administering to the patient and effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a total polyphenol basis.

In another aspect of the invention provides a method for reducing the levels of inflammatory cytokines associated with rheumatoid arthritis, comprising administering to the patient and effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a total polyphenol basis.

In another aspect of the invention provides a method of reducing synovial hyperplasia associated with rheumatoid arthritis, comprising administering to the patient an effective amount of *feijoa* fruit extract, wherein the *feijoa* fruit extract comprises (a) about 40 to about 70 wt %, (preferably about 50 to about 60 wt %) oligomeric proanthocyanidin and (b) about 10 to about 20 wt % ellagitannins, on a total polyphenol basis.

In the above aspects:

In one embodiment, the *feijoa* fruit extract comprises about 60 to about 90% polyphenol compounds, on a dry weight basis.

In one embodiment, the *feijoa* fruit extract comprises about 60 to about 90 wt % polyphenol compounds.

In one embodiment, the patient is administered 150 mg of *feijoa* fruit extract daily.

In one aspect, the invention provides a dosage unit for preventing or treating rheumatoid arthritis, wherein the dosage unit comprises about 150 mg *feijoa* fruit extract.

In one embodiment, the dosage unit is a tablet. In one embodiment, the dosage unit is to be administered daily.

The *feijoa* fruit extract may be administered to a patient by a variety of routes, including orally, parenterally, by inhalation spray, topically, rectally, nasally, buccally or via an implanted reservoir. Preferably, the *feijoa* fruit extract is administered orally, in tablet form. The amount of *feijoa* fruit extract to be administered will vary widely according to the nature of the patient and the nature and extent of the disorder to be treated. Typically the daily dosage of *feijoa* fruit extract for an adult human will be in the range of less than about 1 to about 2000 milligrams, preferably about 0.1 to about 2000 milligrams, more preferably about 0.1 to about 1000 milligrams, more preferably about 50 to about 500 milligrams, more preferably about 100 to about 500 milligrams, more preferably about 150 to about 250 milligrams, most preferably about 150 milligrams. The specific dosage required for any particular patient will depend upon a variety of factors, including the patient's age, body weight, general health, sex, etc.

The invention is further described with reference to the following examples. However, it is to be appreciated that the invention is not limited to these examples.

7. EXAMPLES

Example 1: Preparation of *Feijoa* Fruit Extract

The extract of *feijoa* was prepared and isolated from fresh *feijoa* fruit. Whole *feijoa* fruit, skin, flesh, fruit residues left from juicing operations or various mixtures of these were minced in a blender. To the resulting pulp was added approximately an equal volume of water, alcohol, a water miscible organic solvent such as acetone or an aqueous mixture of alcohol or organic solvent. In this example, food grade ethanol was used. The mixture was stirred occasionally during the first hour and left to soak overnight. The mixture was filtered and the filtrate concentrated at 40° C. under vacuum. The concentrate was filtered to remove any precipitated material and then passed through a column of polymeric resin, Mitsubish, HP20, in this example. Distilled water was passed through the column to remove sugars and other polar materials. The absorbed compounds were eluted from the column with ethanol and concentrated under reduced pressure to give a dark concentrate. The concentrate was freeze-dried to give the *feijoa* fruit extract as a light brown powder. The extract was characterised by HPLC using diode array detection (FIG. 1 and Table 1) and total ion current detection (TOF-MS ES+). A Kinetex 2.6μ. C18 (50×3.0 mm) column is used with a flow rate of 0.3 mL/min at 40° C.

Example 2: Determination of Components of *Feijoa* Fruit Extract

The components of the *feijoa* fruit extract were isolated by repeated preparative column chromatography using size exclusion chromatography on Sephadex LH 20 and Mitsubishi HP20. Their identification was determined by the use of Nuclear magnetic resonance spectroscopy and where necessary the chemical structures of the elucidated components were confirmed by mass spectrometry. A liquid Chromatography-Mass Spectrometry chemical composition profile of the *feijoa* fruit extract was made using Kinetex 2.6μ C18 (50×3.0 mm) column at 40° C. with a flow rate of 0.3 mL/min. The solvent mixture consisted of solvent A ($H_2O$+ 0.1% formic acid) and solvent B (acetonitrile+0.1% formic acid) with the program 0-30 min, 0-100%. Detection was made by diode array and total ion current (TIC). Chromatographic separation of *feijoa* fruit extract led to the isolation and identification of catechin, epicatechin, gallocatechin, procyanidin B2, procyanidin oligomers, ellagic acid, α- and β-pedunculagin as well as other related ellagitannins (FIG. 1 and Table 1).

TABLE 1

| HPLC of feijoa extract | |
|---|---|
| Retention time (mins) | Compound |
| 4.40 | α-pedunculagin |
| 5.30 | β-pedunculagin |
| 5.77 | catechin |
| 6.50 | gallocatechin |
| 6.80 | catechin B2 |
| 6.81 | epicatechin |
| 8.30, 8.77, 9.92 | ellagitannins |
| 5.0-9.0 | procyanidin oligomers |
| 15.3 | flavone |

The various components were identified using the techniques attired below.

Ellagic Acid Determination

This was performed by acid hydrolysis of the *feijoa* fruit extract or concentrate and subsequent analysis of the resulting ellagic acid by HPLC. 80 uL of extract was transferred to a 15 mL glass centrifuge tube, and 250 uL of 2.6 N HCl was added and the tube sealed with a screw cap. The sample was hydrolysed by heating in a water bath at 90 C for 2 hours. The tubes were removed and cooled immediately and stored at 4 C for 1 hour. The hydrolysates were then extracted 2× with ethyl acetate (1 mL). The combined ethyl acetate extracts were dried under nitrogen and taken up in 1 mL methanol which were analysed by HPLC. The major peak in the 360 nm chromatogram (Waters UPLC, Kinetex column, acetonitrile: water gradient each with 0.1% formic acid) was ellagic acid. The levels of ellagic acid were compared with the original extract made up at 4 mg/mL.

HPLC Determination of Pedunculagin, General Ellagic Acid Compounds and Flavone

Pedunculagin exists as two interconverting forms and is generally seen as two major peaks in the early part of the chromatogram. The peak sharpness is enhanced when the samples are prepared in water or 90:10 water:ethanol. The relative pedunculagin content is estimated from the integration of these two peaks in the 280 nm chromatogram.

The general ellagic acid compounds are seen as a set of peaks eluting in the middle of the chromatogram and having absorbance maxima at 360 nm. The relative ellagic acid compound content is estimated from the integration of this set of peaks in the 360 nm chromatogram.

Flavone is a single peak late in the chromatogram with a characteristic uv spectrum. The relative flavone content is estimated from the integration of this peak in the 280 nm chromatogram.

HPLC Determination of Proanthocyanidin Oligomers (PACO)

This complex set of compounds appear in most chromatograms as a hump across much of the chromatogram. However if a special gradient is used the PACO appear as an isolated hump late in the chromatogram. The estimation of PACO content from the peak area under this hump is consistent with measurements made using other techniques. The relative PACO content is estimated from the integration of this hump in the 280 nm chromatogram and comparison.

Colorimetric Determination of Proanthocyanidin Oligomers (PACO)

This determination was performed using the procedure described in Prior R L, Fan E, Ji H, Howell A, Nio C, Payne M J, Reed J. Multi-laboratory validation of a standard method for quantifying proanthocyanidins in cranberry powders. J Sci Food Agric. 2010 90(9):1473-8). The sample wass allowed to react with 4-dimethylaminocinnamaldehyde (DMAC) in acidic ethanol and the coloured product detected by absorption spectroscopy. Samples of the test solutions (70 uL) were placed in one column of the wells of a 96-well microplate and were then diluted across the plate by the addition and mixing of an equal volume of 70:30 ethanol:water. The DMAC reagent (210 uL of 50 mg in 50 mL acidified ethanol solution) was added to each well and the plate immediately placed in the plate reader. The plate reader wass set up to shake the plate and read the absorbance at 640 nm every minute for 30 minutes. The absorbance reading generally reaches a maximum at about 20 minutes. The final readings at 30 minutes were used for the calculations. The dilution curves allowed comparisons to be made for the most appropriate concentration and absorbance (0.2-1.2 A.U.).

Example 3: Immune Function in Mice

The effect of the *feijoa* fruit extract on the immune function in aged mice was evaluated. Aged mice at 48 weeks old, were kept at 20° C. to 22° C. at 50% humidity during the experiment. Mice were divided into 2 groups and fed the following diets: basic diet or basic diet supplemented with the *feijoa* fruit extract at 1.2 mg/day/mouse. The *feijoa* fruit extract was prepared in accordance with Example 1. A third group of young mice were also included for comparison (basic diet only). The amount of food intake and body weight is recorded once a week.

After 32 weeks of feeding, all mice were sacrificed under anaesthesia with Nembutal (0.1 mg/100 g body weight). The spleen is isolated and weighed (Table 2).

TABLE 2

| Mice Group | | | | | |
|---|---|---|---|---|---|
| Mouse Age | Treatment | Body Weight (g) | Spleen (mg) | Liver (g) | Heart (mg) |
| Young | Chow diet | 26.36 ± 3.20 | 89.71 ± 16.25 | 1.46 ± 0.23 | 153.48 ± 14.12 |
| Aged | Chow diet | 43.08 ± 2.30 | 174.95 ± 15.15 | 1.76 ± 0.15 | 163.88 ± 16.81 |
| Aged | Feijoa fruit extract | 44.2 ± 3.1 | 133.5 ± 19.2 | 1.7 ± 0.2 | 160.2 ± 12.9 |

Mice supplemented with Feijoa fruit extract consumed 6 gm food/day, which equates to 1.8 mg of extract/day. The feijoa fruit extract was added to the diet at a dose of 300 mg/kg. Data indicates mean ± SD from 6 mice per group.
*Shows the statistical significance compared to aged control determined by unpaired Students t-test. There were no significant differences in the volume of water and diet consumed during the trial.

ELISA Assay for Cytokines

The production of IL-2, IL-4, IL-6, and IFN-γ from mitogen-stimulated splenocytes was determined as previously described (Chouaib, S.; Welte, K.; Mertelsman, R.; Dupont, B.; J. Immunol., 1985, 135, 1172-1179). Spleens were gently teased with forceps in the culture medium producing a suspension of spleen cells (CM, RPMI 1640 containing 10% fetal bovine serum, 2 mM L-glutamine, $1 \times 10^5$ units/L of penicillin and streptomycin). The red blood cells were lysed with 3 mL of lysing buffer (0.16 mol/L ammonia chloride Tris buffer, pH 7.2) at 37° C. for 5 minutes. The cells were then washed with CM twice. The cell concentrations were counted and adjusted to $2 \times 10^6$ cells/mL. Splenocytes (0.1/well) were cultured in triplicate on 96-well flat-bottom culture plates. Splenocytes (0.1 mL/well) were stimulated with ConA ($1 \times 10^{-2}$ g/L, 0.1 mL/well) to induce IL-2, IL-4 and IFN-γ production. In other plates, splenocytes were cultured with lipopolysaccharide ($1 \times 10^{-6}$ g/L) to induce IL-6 production. These plates were incubated at 37° C., 5% $CO_2$; the culture time for IL-2, IL-4 and IL-6 is 24 hours (or 72 hours for IFN-γ). After incubation, supernatants were collected and stored at −70° C. The cytokines were determined by sandwich ELISA as previously described using a commercial kit.

Mitogenesis of Splenocytes

Splenic T and B-cell proliferation was determined by 3H-thymidine incorporation according to the method previously described (Chouaib, S.; Welte, K.; Mertelsman, R.; Dupont, B.; J. Immunol., 1985, 135, 1172-1179). 0.1 mL splenocytes in CM ($2 \times 10^6$ cells/mL) were cultured in 96-well flat-bottom cultured plates with ConA or LPS (10 μg/mL) or without ConA or LPS (Spontaneous mitogenesis). They were incubated at 37° C., 5% $CO_2$ for 48 hours and then pulsed with 3H-thymidine (0.5/well). After 24 hours, supernatants were harvested by a cell sample harvester.

Vitamin E Measurement

Vitamin E levels in mouse liver were measured by HPLC according to the method described previously (Lee, J., Jiang, S., Liang, B., Inserra, P., Zhang, Z., Solkoff, D., Watson, R. R, Nutr. Res., 1998, 18, 327-339). 0.2 g of tissue was homogenised in 1 mL of water. Butylated hydroxytoluene was added to prevent oxidation of α-tocopherol. α-Tocopherol was extracted from the homogenate using pentanes, ethanol and sodium dodecyl sulfate and concentrated under a steady flow of nitrogen gas at 20° C. The concentrate was redissolved in 0.5 mL of methanol and injected onto a C18 column (3.9×150 mm). A mobile phase composed of methanol: 1 mol/L sodium acetate in the ratio of 97:3 (by volume) at a flow rate of 1.5 mL/min was used. α-Tocopherol, eluted at 22 min and was monitored by a fluorescence detector (Millipore) at 290-nm excitation and 320-nm emission wavelength.

The results indicated that orally ingested *feijoa* fruit extract at a dose of 1.8 mg/day per aged mouse, decreases splenic T-cell production of IL-4, TNF-α and TNF-β. IL-2 and IFN-γ production was not significantly affected in either the control group or the group given the supplement at a dosage of 1.8 mg/day. Splenocyte proliferation when stimulated by ConA at a concentration of 2 μg/mL also decreased. The *feijoa* fruit extract supplementation at an appropriate dose caused significant increases in splenic T-cell immune function in aged mice (Table 3).

TABLE 3

|  | Young Unsupplemented | Aged Unsupplemented | Aged supplemented |
| --- | --- | --- | --- |
| T-cell proliferation (%) (aged unsupplemented = 100) | 130 ± 15* | 100 ± 9 | 78 ± 9* |
| B-cell proliferation (%) (aged unsupplemented = 100) | 130 ± 8* | 100 ± 4 | 85 ± 4* |
| IL-2 level by splenocytes (pg/mL) | 278 ± 26 | 264 ± 38 | 216 ± 47 |
| IFN-γ level by splenocytes (pg/mL) | 1555 ± 12 | 750 ± 37 | 907 ± 12 |
| TNF-α level by splenocytes (pg/mL) | 290 ± 30* | 650 ± 53 | 450 ± 35* |
| TNF-β level by splenocytes (pg/mL) | 95 ± 20* | 142 ± 18 | 70 ± 10* |
| IL-4 level by splenocytes (pg/mL) | 135 ± 40 | 165 ± 45 | 90 ± 30* |
| MDA levels in liver tissue (mol/mg protein) | 0.12 ± 0.02* | 0.325 ± 0.07 | 0.19 ± 0.03* |
| Hepatic vitamin E level (%) (aged unsupplemented = 100) | 200 ± 26* | 100 ± 9 | 177 ± 3* |

Data indicates mean ± SD from 6 mice per group.
*Shows the statistical significance compared to aged control determined by unpaired Students t-test.

Aged mice supplemented with *feijoa* fruit extract at a dosage of 1.8 mg/day showed a decrease in their IL-4 production by 44% (P<0.01) versus the aged unsupplemented group.

Aged mice supplemented with *feijoa* fruit extract showed a 20% decrease in ConA stimulated splenic T-cell mitogenesis vs. aged mice not fed the *feijoa* fruit extract. Similarly, mice supplemented with *feijoa* fruit extract showed a 14% decrease in LPS stimulated splenic B-cell mitogenesis. Aged animals often have spontaneously stimulated B-cells, which do not function as well as those in younger animals and also inhibit T-cells. Therefore, lowering mitogenesis or cell division by B-cells should be beneficial to host defenses.

Immunosenescence (deterioration of the immune system by age advancement) is a major contributing factor in survival to old age or premature death in humans and animals. Some of the adverse effects include dysregulated cell division of T- and B-lymphocytes upon stimulation by mitogens in vitro, or pathogens in vivo with altered cytokine production. In the present studies, B- and T-lymphocytes from aged mice divided less than those of young mice, and those from aged mice fed the *feijoa* fruit extract. The key observations on regulatory cytokines include stimulation of INF-γ, TNF-α, -β and -γ, and IL-4 by consequences of immunosenescence in aging. The lowering of these cytokines due to consumption of dietary *feijoa* fruit extract suggests better overall immune regulation, which can provide improved disease resistance.

Immune regulation during immunosenescent T-cell immune dysfunction seems to be associated in part with the level of vitamin E. Vitamin E reverses age-associated defects in T-cells, particularly naïve T-cells whose levels are greatly reduced in aging. Vitamin E directly affects T-cells as well as PGE2 inhibition. Without wishing to be bound by theory, the applicant hypothesises that the beneficial effects of *feijoa* fruit extract supplementation that are observed on immunosenescence that cause T-cell immune dysfunction could be due, in part to its ability to conserve cellular vitamin E level. Aged mice supplemented with *feijoa* fruit extract showed a 77% increase in the level of hepatic vitamin E when compared to the aged unsupplemented test group (Table 3). *Feijoa* fruit extract also lowered TNF-α which is known to be elevated in aging. Thus *feijoa* fruit extract has beneficial influence in moderating immune functions in the aged.

Example 4: Human Clinical Trial to Measure Hypertension, Hyperlipidaemia, and Hyperglycaemia The study population consisted of men and women, 40-75 years of age, with non-insulin dependent Type-2 diabetes. Exclusion criteria included Type-1 diabetes; use of any supplements other than single daily multivitamin; having any major illness such as cancer, asthma, or heart failure; any previous cardiac events; pregnancy, or being a nursing mother. The protocol of this 12-week, randomised, double-blind, placebo-controlled trial was approved by the institutional review board at Mashad University and performed in accordance with the Declaration of Helsinki. Study subjects were recruited by the university diabetes clinic. All subjects gave written informed consent before participation in this research trial. Subjects were randomly assigned to receive either *feijoa* fruit extract (150 mg, once a day) in the form of a pill or a matched placebo, both of which remain constant throughout the study period. The *feijoa* extract was prepared according to the process set out in Example 1.

TABLE 4

Feijoa fruit extract: Human participant study.

|  | Placebo | Feijoa fruit extract |
| --- | --- | --- |
| Number of participants | 14 | 20 |
| Male:female ratio | 7:7 | 4:16 |
| Age (years) | 52.6 | 55.0 |
| Weight (kg) | 77.6 | 77.2 |
| Height (cm) | 164.4 | 158.6 |

Participants received 150 mg/person/day of the feijoa fruit extract. As shown in Table 4 above, the demographic and clinical characteristics are similar. Mean years of diabetes treatment was the same for both groups. 19 of the 20 subjects supplemented with feijoa extract used additional medication: 95% used a combination of Metformin and Glibenclamide with two participants using insulin. 13 of the 14 subjects in the placebo group used additional medication: 55% used Metformin and Glibenclamide, insulin (1 subject) or Atenolol.

Blood pressure and heart rate were recorded at baseline and after 12 weeks. Blood pressure and heart rate were measured on the left arm after 10 min rest. Korotkoff sounds I and V were taken as the systolic and diastolic blood pressures, respectively. Repeated readings were taken at 2-minute intervals for a total of 3 sitting measurements and the average was recorded. All treatments including anti-diabetic medications remained constant throughout the study period. Unused pills were collected and counted at monthly follow-up visits to assess participant compliance. Changes in concomitant medications and clinical adverse effects at follow up visits were investigated by questioning the participants, none were reported.

Analysis was performed according to the intention to treat principle. Thus all randomised patients who received at least one dose of study treatment and who have both a baseline and at least one post-baseline measurement were analysed. The data are expressed as mean±SEM. Statistical analyses are performed with SPSS version 11.5 (SPSS Institute, Chicago, Ill.) (Sprinthall R. C., Basic statistical analysis, Boston: Allyn and Bacon; 2003, 550-565). Chi-square test with Yates' correction is used for non-continuous variables for the prevalence study. Student's t-test is used to assess the statistical significance of the continuous variables. Comparable nonparametric test (Mann-Whitney U test) is substituted when tests for normality and equal variance failed. A value of $P<0.05$ was used as a criterion for statistical significance. Trial participants showed no significant changes in the standard liver enzyme profile due to the *feijoa* fruit extract. In addition, there is no significant difference in serum creatinine, albumin, and urea (data not shown) due to the *feijoa* fruit extract. These data suggest no toxicity occurs.

Initial systolic blood pressure was comparable for the placebo group and the group supplemented with *feijoa* fruit extract. There were no significant differences observed in HDL cholesterol and diastolic blood pressure. The intake of the *feijoa* fruit extract induced a decrease in systolic blood pressure in comparison with the placebo group which showed an increase ($P<0.0776$). This indicated an improvement of systolic blood pressure control with *feijoa* fruit extract at the end of the 12 week trial period when compared to placebo (Table 5). Comparatively, diastolic blood pressure levels trended lower in the group receiving the *feijoa* fruit extract while the placebo group increased ($P<0.35$).

Supplementation with *feijoa* fruit extract also reduced the values of several serum variables which were used to assess the health status of diabetics. Subjects receiving the *feijoa* fruit extract showed a reduction in fasting serum glucose whereas the placebo group showed an increase ($P<0.0001$) (Table 5). Significant changes to HbA1c levels were also observed by the $12^{th}$ week of the trial. Mean HbA1c levels in the *feijoa* fruit extract treated group decreased while the levels in the placebo group increased ($P<0.0001$) (Table 5). In addition, at the end of the 12-week trial period, patients supplemented with *feijoa* fruit extract show a marked decrease in serum triglycerides ($P<0.0127$), serum total cholesterol ($P<0.0887$) and LDL-cholesterol ($P<0.157$) (Table 5). In summary, these data show that *feijoa* fruit extract can improve diabetes control, reduce antihypertensive medicine use, and may favour a reduction in cardiovascular disease risk in individuals with Type-2 diabetes.

Example 5: Obesity Study Using Obese Mice

Male leptin-deficient (ob/ob) obese mice (5 weeks old, 26~33 g) and lean C57BL/6J wild type (WT) mice were purchased from SLC, Inc. (Hamamtsu, Japan). The mice were housed in temperature ($22\pm2°$ C.), humidity ($50\pm5\%$) and light (12 hr light/dark cycles) controlled conditions. The animals were allowed to acclimatize for 1 week prior to experiments. Then the mice were randomly divided into three groups of 6 mice. Negative control (genetically normal control, C57BL/6J) and positive control (ob/ob control) groups were fed normal American Institute of Nutrition (AIN) 93M diet, and the other group was fed AIN93M diet containing *feijoa* extract at 300 mg/kg diet for 16 weeks. The *feijoa* fruit extract prepared in accordance with Example 1 was mixed homogenously into the powdered diet and the diet was given in the solid form. Body weight is measured at the beginning of the experiment and weekly intervals for the 16 week study period. The amount of food consumed by each group was recorded on a daily basis.

After 16 weeks on experimental diets, the mice were sacrificed and tissues are collected for analysis. Blood was collected, dispensed into serum tubes and centrifuged for 20 min at 1,600 rpm. The serum triglyceride and total cholesterols levels were analysed by commercial kits (Cayman Chemical, Ann Arbor, Mich., USA) and high-density lipoprotein-cholesterol were measured fluorimetrically with quantitation kit (BioVision Research Products, Mountain View, Calif., USA).

TABLE 5

The effect of feijoa fruit extract in human subjects with Type-2 diabetes.

| | Placebo | | | Feijoa fruit extract | | |
|---|---|---|---|---|---|---|
| Variable | Baseline | Week 12 | Change | Baseline | Week 12 | Change |
| Triglycerides (mg/dL) | 208.2 ± 23.5 | 241.9 ± 29.7 | +33.6 ± 12.6 | 197.9 ± 28.1 | 159.8 ± 20.8* | −38.1 ± 20.9 |
| Glucose (mg/dL) | 168.4 ± 8.4 | 181.9 ± 10.3 | +13.5 ± 30.7 | 184.0 ± 8.2 | 147.7 ± 8.0*† | −36.3 ± 2.7 |
| HbA1c (%) | 7.5 ± 0.4 | 8.1 ± 0.4 | +0.49 ± 0.19 | 8.6 ± 0.3 | 7.7 ± 0.2* | −0.86 ± 0.14 |
| LDL-cholesterol (mg/dL) | 109.3 ± 37.2 | 116.1 ± 40.3 | +6.8 ± 7.5 | 105.2 ± 15.2 | 87.2 ± 8.7 | −18.1 ± 14.4 |
| Serum cholesterol (mg/L) | 194.8 ± 9.6 | 209.8 ± 10.1 | 15.0 ± 9.8 | 201.1 ± 9.9 | 183.6 ± 7.3 | −17.5 ± 6.9 |
| Systolic BP (mmHg) | 144.2 ± 0.2 | 142.9 ± 0.5 | +0.36 ± 1.5 | 144.3 ± 1 | 137.6 ± 1.3 | -6.7 ± 2.7 |

Analysed by Student's t-test,
*P <.001 compared with the baseline,
†P <.001 compared with the placebo group.
Measurements were performed on serum samples after 8-hours of fasting at the baseline and after 12 weeks of treatment.
Values are means ± SEM (n = 20 subjects in feijoa fruit extract group and 14 in placebo except for LDL-cholesterol when both groups are 6).

The changes in body weight during the experimental period due to the effect of *feijoa* fruit extract are shown in Table 6. *Feijoa* fruit extract supplementation significantly decreased the amount of weight gained by 24% when compared to the control in ob/ob mice. Throughout the experiment, the food intake was higher for the obese control group than in the control group. However, the obese mice in both the control group and *feijoa* fruit extract supplemented group consumed similar volumes of food. The food efficiency ratio significantly decreased in a *feijoa* fruit extract supplementation group compared to obese control group.

TABLE 6

Body Weight Changes in Obese Mice.

|  | Normal mice control | Ob/ob control (obese) | Feijoa fruit extract treated ob/ob mice |
|---|---|---|---|
| Initial body weight (g) | 21.79 ± 1.09* | 32.45 ± 2.15 | 34.40 ± 1.96 |
| Final body weight (g) | 37.29 ± 3.11* | 65.23 ± 3.97 | 59.05 ± 2.72* |
| Weight gain (g/day) | 0.14 ± 0.03* | 0.29 ± 0.05 | 0.22 ± 0.04* |
| Food Intake (g/day) | 3.53 ± 0.35* | 5.28 ± 0.39 | 4.89 ± 0.58 |
| Food efficiency ratio (body weight gain/ food intake) × 100 | 3.90 ± 0.49* | 5.51 ± 0.57 | 4.49 ± 0.37* |
| Heart weight (g) | 0.13 ± 0.01 | 0.13 ± 0.01 | 0.13 ± 0.01 |
| Kidney weight (g) | 0.22 ± 0.02* | 0.27 ± 0.02 | 0.25 ± 0.02 |
| Liver weight (g) | 1.89 ± 0.17* | 4.44 ± 0.39 | 3.97 ± 0.31* |
| Spleen weight (g) | 0.07 ± 0.01 | 0.07 ± 0.01 | 0.06 ± 0.01 |
| Retroperitoneal adipose tissue weight (g) | 0.53 ± 0.19* | 3.15 ± 0.46 | 2.63 ± 0.36 |
| Epididymal adipose tissue weight (g) | 1.58 ± 0.26* | 4.23 ± 0.36 | 3.63 ± 0.43* |

Values are means ± SD from 6 mice/group.
Mean with * indicates a significant difference at $p < 0.05$, compared to negative control.

In the *feijoa* fruit supplemented group, the weights of the heart, kidney, and spleen were not significantly different when compared to control group (Table 6). In mice supplemented with *feijoa* fruit extract, the weight of the liver was 10.6% less than that of the control group. In order to examine the effect of *feijoa* supplementation on body fat accumulation, the weight of adipose tissue in ob/ob mice was measured. The weights of retroperitoneal and epididymal adipose tissues were significantly higher in the ob/ob control group when compared to normal control mice. The weight of epididymal adipose tissue in the *feijoa* fruit extract group was significantly lower than the ob/ob control group. However, the supplementation of *feijoa* fruit extract did not appear to have an effect on retroperitoneal adipose tissue in the *feijoa* fruit extract supplemented group when compared to the obese mice.

It was also found that the ob/ob control group had significantly elevated serum total cholesterol and triglyceride levels when compared to the normal control group. However, it was found that supplementation with *feijoa* fruit extract did not affect the serum total cholesterol and triglyceride levels. In addition, HDL-cholesterol levels were not changed by supplementation of *feijoa* fruit extract compared to ob/ob control group. Supplementation in the diet of obese mice with the *feijoa* fruit extract was found to reduce the hepatic total cholesterol level compared to the ob/ob control mice; however the hepatic triglyceride level was not affected.

Obese mice fed a diet supplemented with *feijoa* fruit extract did not gain as much body weight, showed a lower food efficiency ratio, and exhibited significant beneficial changes in hepatic total cholesterol levels. This tendency is presumed to relate to the suppression of lipid accumulation in adipose tissues. Thus, dietary supplementation of *feijoa* fruit extract may physically affect body weight gain and reduce fat tissue accumulation.

Example 6: Arthritis Studies Using Collagen-Induced Arthritis Mice

Figure 2:
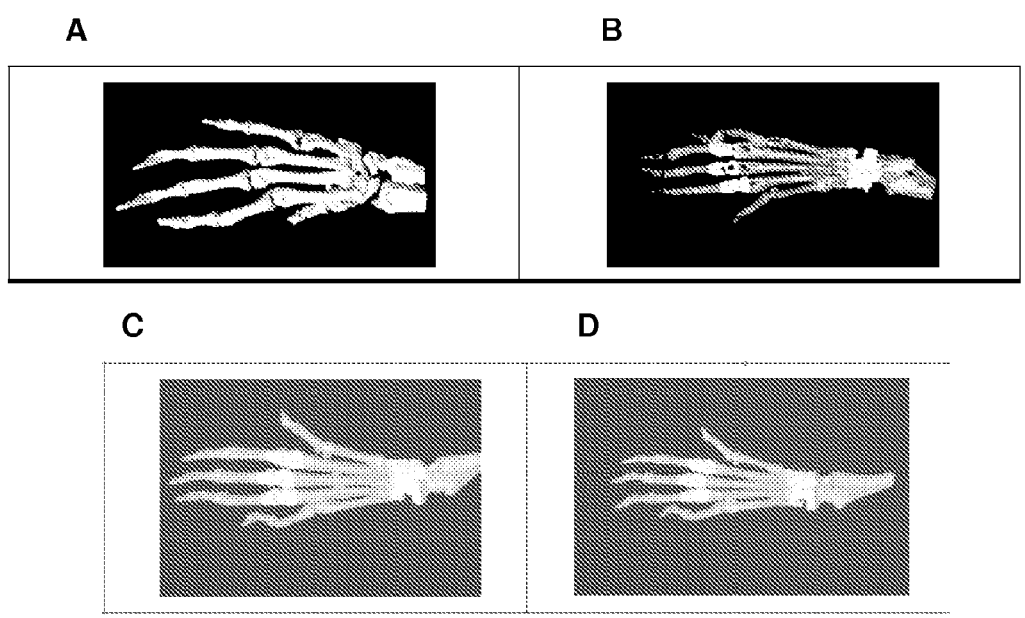
FIG. 2 shows the radiological images of the paws of (A) normal control, (B) arthritic control, (C) methotrexate-treated and (D) *feijoa* fruit extract-supplemented mice in the collagen-induced arthritis mouse study (Example 6).

Male DBA/1J mice (6 weeks old, 20~22 g) were purchased from Japan SLC, Inc. (Shizoka, Japan). The mice were divided into 4 groups of 5 mice per group and were fed American Institute of Nutrition 93G diet and water ad libitum at a temperature of 25° C. at relative humidity of 55%. Mice were maintained in a 12 hour light/dark cycle under specific pathogen-free conditions according to the institutional instructions of Kyung Hee University, Korea. All animal experiments were performed in accordance with ethical guidelines issued by the Animal Care and Use committee of the College of Medicine, Seoul National University (Seoul, Korea). The 4 groups were normal control (no collagen-induced arthritis, no dietary supplementation), negative control (collagen-induced arthritis receiving no dietary supplement), positive control (collagen-induced arthritis diet supplemented with 10 mg/kg methotrexate) and *feijoa* fruit extract supplemented (collagen-induced arthritis, diet supplemented with *feijoa* fruit extract powder). The body weights between the mice groups did not show any significant differences. There were no significant differences between the volumes of food and water that are consumed between the groups. This indicates that changes in experimental data were not due to either body weight or water and food consumption. An average 25 g mouse consumed approximately 6 g of diet per day, consuming 1.8 mg of *feijoa* fruit extract. Arthritis was induced by injecting 0.1 ml of bovine Type II collagen (Chondrex, Inc., Redmond, Wash., USA) was dissolved in 10 mM acetic acid at concentration of 2 mg/mL by stirring overnight at 4° C. The collagen was emulsified in an equal volume of complete Freund's adjuvant containing *Mycobacterium tuberculosis* in an ice-cold water bath. Mice are injected subcutaneously at the base of the tail with 0.1 mL of emulsion. The mice were given a booster collagen injection on day 21 with incomplete Freunds adjuvant of 0.1 ml of emulsion. Clinical assessment of inflammation on the paws of the mice was visually performed 3 times weekly between day 56 and day 79 using a 4-point scale (0-4) for each paw (Table 1). The total score for clinical assessment was measured on each mouse (4 points per paw with maximum score of 16). A mouse modular treadmill with 10 inches of running surface made by Columbus Instruments (USA) was used. The speed is adjusted from 6-100 meters per minute to assess the mouse's maximum speed ability. Running speed and foot pressure measurements were performed 3 times weekly from day 56 until day 79. The mice were sacrificed at the end of the trial. The knees of the mice were removed, frozen, and later sectioned. They are stained with hematoxylin and eosin and photographed as shown in FIG. 2. The hind paws are structurally assessed with X-ray micro computerised tomographic imaging within inflamed joints and are photographed with intensity shown in colour. They were perfused with radiopaque silicone rubber, the uptake of silicon is measured by X-ray micro CT at 21 μm resolution and images were analyzed in 3-D using custom software and laboratory micro-CT scanner consisting of a tungsten-anode X-ray tube with a relatively small focal spot (~10 μm), coupled to a high-resolution X-ray detector system (~50 μm pixel spacing). Uptake of the radiopaque silicone rubber reduces X-ray penetration and changes colour intensity.

The progression of arthritis was assessed by subjecting mice to a treadmill test and comparing the levels of inflammation between all groups (Table 7 and Table 8). Slower running speeds and lighter foot pressures are indicative of inflammation and an attempt by the mouse to reduce any pain. As shown in Table 7, subjects treated with *feijoa* fruit extract showed beneficial clinical scores when compared to the arthritic control and a similar value when compared to the methotrexate treated group. As expected, running speed was highest in normal control group, and lowest in the arthritis-induced control group (Table 8). Surprisingly and advantageously there was no significant difference between the methotrexate and the *feijoa* fruit extract treated group.

TABLE 7

Assessment of feijoa fruit extract on paw swelling in arthritis induced mice

|  | Normal control | Arthritic control | Methotrexate treated | Feijoa fruit extract |
| --- | --- | --- | --- | --- |
| Clinical Score | 11.2 ± 0.7* | 5.5 ± 1.2 | 10.5 ± 0.7* | 9.5 ± 2.0* |

*indicates a statistical significance determined by student's t-test compared to arthritic control

TABLE 8

Effects of Feijoa fruit extract on running speed and foot pressure

| Treadmill Results | Running Speed (mm/s) | Foot pressure |
| --- | --- | --- |
| Normal control | 133.05 ± 3.72* | 148.54 ± 2.39* |
| Arthritic control | 91.24 ± 2.59 | 136.89 ± 0.85 |
| Methotrexate treated | 121.36 ± 1.69* | 141.23 ± 5.28* |
| Feijoa fruit extract | 120.54 ± 5.42* | 143.97 ± 3.69* |

Values are means ± SD from 5 mice/group.
*indicates a significant difference at $p < 0.05$, compared to negative control.

Figure 3:
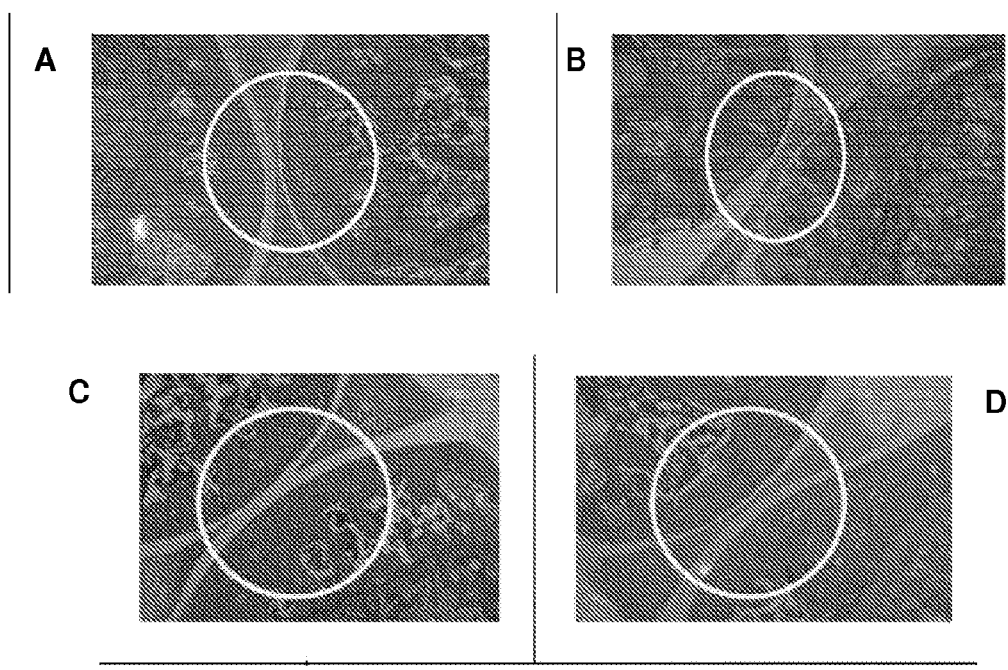
FIG. 3 shows histological images after hematoxylin and eosin (H&E) staining of the joint sections of the paws of (A) normal control, (B) arthritic control, (C) *feijoa* fruit extract-supplemented and (D) methotrexate-treated mice in the collagen-induced arthritis mouse study (Example 6).

The mice were sacrificed at the end of the trial period and the joints examined for the progression of arthritis. Histological evaluation of the joint sections of CIA mice showed decreased synovial hyperplasia (an increase in destructive cytokine production in synovial fluid) (FIG. 3). In contrast, the *feijoa* fruit extract and methotrexate treated groups had relatively normal joint structures with little soft tissue swelling (FIGS. 2, 3), while normal control showed no synovial thickening or inflammatory cell infiltration, and the joint structures were well maintained. Since synovial hyperplasia results in bone and cartilage erosion which can facilitate the onset of rheumatoid arthritis, the reduction observed in the *feijoa* extract supplemented mice compared to the arthritic control suggests that the extract is beneficial in reducing the effects and onset of rheumatoid arthritis.

Radiologic studies revealed that there was no evidence of joint deformity or soft tissue swelling in the normal control. Severe joint destruction along with soft tissue swelling was observed in the arthritic control group; however, members of the *feijoa* treated group have relatively normal joint structures with little soft tissue swelling which was comparable with the methotrexate group of mice.

To establish whether the protective effect of the *feijoa* fruit extract was related to the anti-inflammatory response observed in the CIA mice, pro-inflammatory cytokines (TNF-α, IL-2 and INF-γ) were investigated using the ELISA assay described in Example 3 (Table 9). It is well known that such cytokines play crucial roles in joint destruction by damaging the synovial cells within the joint. Consequently, a reduction in synovial cells within the joint results in an increase in friction, which in turn, results in inflammation and the potential development of arthritis. As shown in Table 9, the *feijoa* fruit extract treated group had significantly lower levels of pro-inflammatory cytokines when compared to the arthritic control and showed comparable values when compared to mice treated with methotrexate. Supplementation with *feijoa* fruit extract resulted in significant decreases in IL-2 and IFN-γ levels by 48% and 40% respectively when compared to the arthritic control group, indicating reduced destruction within the joint.

TABLE 9

Cytokine data for CIA mice.

|  | Normal control | Arthritic control | Methotrexate treated | Feijoa fruit extract |
| --- | --- | --- | --- | --- |
| TNF-α level by splenocytes (pg/mL) | 200 ± 22 | 536 ± 60 | 255 ± 15* | 233 ± 46* |
| IL-2 level by splenocytes (pg/mL) | 50 ± 16 | 151 ± 12 | 104 ± 10 | 90 ± 8* |
| IFN-γ level by splenocytes (pg/mL) | 76 ± 12 | 394 ± 76 | 182 ± 21* | 200 ± 14* |

Values are means ± SD from 5 mice/group.
Mean with * indicates a significant difference at $p < 0.05$, compared to arthritic control.

Although the invention has been described by way of example, it should be appreciated that variations and modifications may be made without departing from the scope of the invention.

Furthermore, where known equivalents exist to specific features, such equivalents are incorporated as if specifically referred to in the specification.

What we claim is:

1. A method of:
   preventing or treating hyperglycaemia in a patient; or
   preventing or ameliorating one or more symptoms of diabetes associated with hyperglycaemia in a patient;
   comprising administering to the patient an effective amount of *feijoa* fruit extract, thereby:
   preventing or treating hyperglycaemia in the patient, or
   preventing or ameliorating the one or more symptoms of diabetes associated with hyperglycaemia in the patient.

2. The method of claim 1, wherein the patient's serum glucose is lowered.

3. The method of claim 2, wherein HbA1c levels in the patient are reduced.

4. The method of claim 2, wherein the patient is a human patient with Type-2 diabetes.

5. The method of claim 1, wherein the *feijoa* fruit extract comprises one, two, or more compounds selected from the group consisting of: catechin, epicatechin, gallocatechin, proanthocyanidins, flavone, ellagic acid, pedunculagin, and other *feijoa* fruit ellagitannins.

6. The method of claim 1, wherein the *feijoa* fruit extract comprises flavones and/or pedunculagin.

7. The method of claim 1, wherein the *feijoa* fruit extract comprises a whole fruit extract.

8. The method of claim 1, wherein the *feijoa* fruit extract is prepared by extraction with water or by extraction with a combination of water and ethanol.

9. The method of claim 1, wherein the *feijoa* fruit extract is prepared by a process including the steps of:
   (i) contacting *feijoa* fruit, or *feijoa* fruit skin, or *feijoa* fruit pulp or residues of *feijoa* fruit from *feijoa* fruit juicing, with water or a combination of water and ethanol to provide an aqueous extract, or aqueous/hydrophilic extract, and a solid residue;

(ii) separating the aqueous extract, or aqueous/hydrophilic extract, from the solid residue to give a crude aqueous *feijoa* fruit extract, or a crude aqueous/hydrophilic *feijoa* fruit extract;

(iii) evaporating the crude aqueous *feijoa* fruit extract, or crude aqueous/hydrophilic *feijoa* fruit extract from step (ii) to give a substantially aqueous *feijoa* fruit extract concentrate and a precipitate;

(iv) separating the substantially aqueous *feijoa* fruit extract concentrate from the precipitate; and (v) fractionating the substantially aqueous *feijoa* fruit extract concentrate from step (iv) to concentrate at least one component thereof.

10. The method of claim 9, wherein the *feijoa* fruit extract comprises flavone and/or pedunculagin.

11. The method of claim 9, wherein the *feijoa* fruit extract comprises at least about 70 weight percent polyphenol compounds, or at least about 80 weight percent polyphenol compounds.

12. The method of claim 9, wherein the *feijoa* fruit extract is formulated as a nutraceutical or pharmaceutical composition comprising the *feijoa* fruit extract and one or more nutraceutical or pharmaceutically acceptable excipients.

13. The method of claim 9, wherein the *feijoa* fruit extract is formulated as a dosage unit comprising:

(i) about 50 mg to about 500 mg *feijoa* fruit extract, or (ii) about 150 mg *feijoa* fruit extract, wherein the *feijoa* fruit extract is formulated as a powder.

14. A method of treating or preventing Type-2 diabetes in a patient comprising administering to the patient the *feijoa* fruit extract prepared by extraction with water or by extraction with a combination of water and ethanol, wherein the *feijoa* fruit extract comprises a whole fruit extract, thereby treating or preventing the Type-2 diabetes in the patient.

15. The method of claim 14, wherein the *feijoa* fruit extract comprises flavone and/or pedunculagin.

16. The method of claim 14, wherein the *feijoa* fruit extract comprises at least about 70 weight percent polyphenol compounds, or at least about 80 weight percent polyphenol compounds.

17. The method of claim 14, wherein the *feijoa* fruit extract is formulated as a dosage unit comprising:

(i) about 50 mg to about 500 mg *feijoa* fruit extract, or (ii) about 150 mg *feijoa* fruit extract, wherein the *feijoa* fruit extract is formulated as a powder.

* * * * *